US008751168B2

(12) United States Patent
Billinge et al.

(10) Patent No.: US 8,751,168 B2
(45) Date of Patent: Jun. 10, 2014

(54) X-RAY CHARACTERIZATION OF SOLID SMALL MOLECULE ORGANIC MATERIALS

(75) Inventors: Simon Billinge, Brooklyn, NY (US); Kenneth Shankland, Reading (GB); Norman Shankland, Glasgow (GB); Alastair Florence, Glasgow (GB)

(73) Assignee: The Trustees of Columbia University in the City of New York, New York, NY (US)

( * ) Notice: Subject to any disclaimer, the term of this patent is extended or adjusted under 35 U.S.C. 154(b) by 369 days.

(21) Appl. No.: 12/802,064

(22) Filed: May 28, 2010

(65) Prior Publication Data

US 2011/0106455 A1 May 5, 2011

Related U.S. Application Data

(60) Provisional application No. 61/217,785, filed on Jun. 3, 2009, provisional application No. 61/271,688, filed on Jul. 24, 2009.

(51) Int. Cl.
*G01N 31/00* (2006.01)

(52) U.S. Cl.
USPC ............... 702/28; 702/19; 702/32; 702/128; 702/179

(58) Field of Classification Search
USPC ............... 702/19, 28, 32, 128, 179; 436/57; 378/88; 365/106
See application file for complete search history.

(56) References Cited

U.S. PATENT DOCUMENTS

| | | | |
|---|---|---|---|
| 5,364,797 A | 11/1994 | Olson et al. | |
| 5,434,330 A * | 7/1995 | Hnatow et al. | 585/864 |
| 6,430,256 B1 | 8/2002 | Yacoby | |
| 6,627,760 B1 | 9/2003 | Roberts | |
| 7,039,161 B2 | 5/2006 | Ito et al. | |
| 2004/0166155 A1 | 8/2004 | Dobetti et al. | |
| 2006/0088473 A1 | 4/2006 | Dowding et al. | |
| 2007/0110214 A1 | 5/2007 | Bates | |
| 2007/0243620 A1 | 10/2007 | Bates et al. | |
| 2008/0065418 A1 | 3/2008 | Byrom et al. | |

OTHER PUBLICATIONS

Billinge et al., "Beyond crystallography; the study of disorder, nanocrystallinity and crystallography challenged materials with pair distribution functions," Chem. Commun., vol. 7, pp. 749-760 (2004).
David et al., "Crystal structure and bonding of ordered C60," Nature, vol. 353, pp. 147-149 (1991).
Hu et al., "Local intermolecular correlation in C60," Physical Review B., vol. 45, No. 16, pp. 9517-9520 (1992).
Juhás et al., "Ab initio determination of solid-state nanostructure," Nature, vol. 440, pp. 655-658 (2006).

(Continued)

*Primary Examiner* — Elias Desta
(74) *Attorney, Agent, or Firm* — Lisa A. Chiarini; Walter M. Egbert, III; Hughes Hubbard & Reed LLP

(57) ABSTRACT

The present invention provides, inter alia, methods of characterizing a small molecule organic material, e.g., a drug or a drug product. This method includes subjecting the solid small molecule organic material to x-ray total scattering analysis at a short wavelength, collecting data generated thereby, and mathematically transforming the data to provide a refined set of data.

26 Claims, 7 Drawing Sheets

(56) References Cited

OTHER PUBLICATIONS

Schmidt et al., "Electron diffraction, X-ray powder diffraction, lattice energy minimisation, and pair distribution function analysis to determine the crystal structures of pigment Yellow 213, C23H21O9N5," Book of Abstracts: the 11th European Powder Diffraction Conference, p. 31 (2008).

Andronis et al., "Crystal Nucleation and Growth of Indomethacin Polymorphs from the Amorphous State," Journal of Non-Crystalline Solids, vol. 271, pp. 236-248 (2000).

Barr et al., "PolySNAP: a computer program for analysing high-throughput powder diffraction data," J. Appl. Cryst., 37, pp. 658-664 (2004).

Bates et al., "Analysis of Amorphous and Nanocrystalline Solids from Their X-Ray Diffraction Patterns," Pharmaceut. Res., vol. 23, No. 10, pp. 2333-2349 (2006).

Bates et al., "Assessment in Defects and Amorphous Structure Produced in Raffinose Pentanhydrate upon Dehydration," Journal of Pharmaceutical Sciences, vol. 96, No. 5, pp. 1418-1433 (2007).

Billinge et al., "The Problem with Determining Atomic Structure at the Nanoscale," Science, vol. 316, pp. 561-565 (2007).

Billinge, "Nanoscale Structural Order from the Atomic Pair Distribution Function (PDF): There's Plenty of Room in the Middle," J. Solid State Chem., vol. 181, pp. 1695-1700 (2008).

Bruehne et al., "PDF from X-Ray Powder Diffraction for Nanometer-Scale Atomic Structure Analysis of Quasicrystalline Alloys," Z. Kristallogr., 220, pp. 962-967 (2005).

Chamarthy et al., "The nature of crystal disorder in milled pharmaceutical materials," Colloids and Surfaces A: Physiochem. Eng. Aspects, 331, pp. 68-75 (2008).

Chupas et al., "Rapid-acquisition pair distribution function (RA-PDF) analysis," J. Appl. Cryst., 36, pp. 1342-1347 (2003).

Farrow et al., "Relationship Between the Atomic Pair Distribution Function and Small Angle Scattering: Implications for Modeling of Nanoparticles," Acta Cryst., A65, pp. 232-239 (2009).

Heinz et al., "Characterizing an Amorphous System Exhibiting Trace Crystallinity: A Case Study with Saquinavir," Crystal Growth & Design, vol. 8, No. 1, pp. 119-127 (2008).

Kodama et al., "Finite Size Effects of Nanoparticles on the Atomic Pair Distribution Functions," Acta Crystal., A62, pp. 444-453 (2006).

Masadeh et al., "Quantitative Size-Dependent Structure and Strain Determination of CdSe Nanoparticles Using Atomic Pair Distribution Function Analysis," Physical Review, B76, 1154131-1-115413-11 (2007).

Nollenberger et al., "Pair Distribution Function X-Ray Analysis Explains Dissolution Characteristics of Felodipine Melt Extrusion Products," Journal of Pharmaceutical Sciences, vol. 98, No. 4, pp. 1476-1486 (2009).

Petkov, "RAD, A Program for Analysis of X-Ray Diffraction Data from Amorphous Materials for Personal Computers," J. Appl. Cryst., 22, pp. 387-389 (1989).

Petkov et al., "High Real-Space Resolution Measurement of the Local Structure of Ga1-xInxAs Using X-Ray Diffraction," Phys. Rev. Lett., vol. 83, No. 20, pp. 4089-4092 (1999).

Petkov et al., "Polyhedral Units and Network Connectivity in Calcium Aluminosilicate Glasses from High-Energy X-Ray Diffraction," Phys. Rev. Lett., vol. 85, No. 16, pp. 3436-3439 (2000).

Qiu et al., "PDFgetX2: a GUI-Driven Program to Obtain the Pair Distribution Function From X-Ray Powder Diffraction Data," J. Appl. Cryst., 37, p. 678 (2004).

Rietveld, "A Profile Refinement Method for Nuclear and Magnetic Structures," J. Appl. Cryst., 2, pp. 65-71 (1969).

Schmidt et al., "Crystal Structures of Pigment Red 170 and Derivatives, as Determined by X-Ray Powder Diffraction," Angew. Chem. Int. Ed., 45, pp. 1313-1317 (2006).

Schmidt et al., "Electron Diifraction, X-Ray Powder Diffraction and Pair-Distribution-Function Analyses to Determine the Crystal Structures of Pigment Yellow 213, C23H21N5O9," Acta Cryst., B65, pp. 189-199 (2009).

Shalaev et al., "The Concept of 'Structure' in Amorphous Solids From the Perspective of the Pharmaceutical Science," Amorphous Food and Pharmaceutical Systems, pp. 11-30, Royal Society of Chemistry, ed. H, Levin, Cambridge (2002).

Wright, "Diffraction Studies of Glass Structure: The First 70 Years," Glass Physics & Chemistry, vol. 24, No. 3, pp. 148-179 (1998).

* cited by examiner

System For Characterizing A Solid
Small Molecule Organic Material (100)

Stretch

X-RAY CHARACTERIZATION OF SOLID SMALL MOLECULE ORGANIC MATERIALS

CROSS-REFERENCE TO RELATED APPLICATIONS

This application claims benefit to U.S. Provisional Patent Application Ser. No. 61/217,785, filed Jun. 3, 2009 and U.S. Provisional Patent Application Ser. No. 61/271,688, filed Jul. 24, 2009. The entire contents of the above-mentioned applications are hereby incorporated by reference as if recited in full herein.

GOVERNMENT FUNDING

This invention was made with government support under DE-AC02-98CH10886 awarded by the U.S. Department of Energy. The government has certain rights in the invention.

FIELD OF THE INVENTION

The present invention relates, inter alia, to characterization of solid small molecule organic material using x-ray total scattering analysis.

BACKGROUND OF THE INVENTION

The knowledge of structure of materials at an atomic-scale level is a prerequisite to understanding material properties in general. The properties of materials are not only determined by their chemical composition, but also chemical structure of the individual molecules, as well as how these molecules are held together to form the material. Thus, even if the individual molecules of two solid materials are identical, the properties of the two materials, such as crystal lattice energies, melting points, chemical reactivity, density and solubilities, may vary widely depending on the solid-state structure of the materials, or how the molecules are arranged or packed over the longer range.

More importantly, in the area of pharmaceuticals, these differences in property may have an important impact on the performance of drugs, such as stability and bioavailability, which refers to the rate and extent to which the active ingredient or active moiety is absorbed from a drug product and becomes available at the site of action. For a drug that is not administered at the site of action or injected directly into the circulatory system, the bioavailability of that drug is generally determined by its solubility and its permeability through a patient's gastrointestinal membrane. A major cause of poor bioavailability of a drug is usually due to poor solubility. The spatial arrangement of the molecules affects solubility, because the crystal lattice structure (if there is any) has to be disrupted by the solvent before the drug can dissolve. For example, if the molecules of a drug are held together tightly to the crystal latter, the drug is less likely to dissolve.

Currently, most drugs are delivered in the form of crystalline powders. There is growing interest in the possibility of administering pharmaceutical drugs in non-crystalline forms, such as amorphous (a-) or nanocrystalline (n-) forms. This is attractive in cases where the crystalline forms are highly insoluble, but the a- or n-forms have greater solubility. However, the very fact that a-forms or n-forms are readily soluble also means that they are less stable. They may crystallize into the stable form during manufacturing, packaging, distribution, or storage of the drugs. Change in the solid state form may lead to unexpected changes in behavior of drugs. This change is a major concern of the pharmaceutical industry because it has considerable formulation and therapeutic implications.

Recently, a completely new avenue has been explored to administer drugs in nanocrystalline form. In this case, the structure of the solid is intermediate between a crystalline powder, where the packing of the molecules is long-range ordered, and the amorphous state, where the packing has only short-range order over a range of 10 Å or so. In this case, local packing of the molecules is quite well defined, as in the crystal, but the range of structural coherence, or order, persists only on the scale of 10's to 100's of nanometers. The nanocrystalline case presents a special appeal because the stability and solubility of the drug is expected to be intermediate between the more stable crystalline and less stable amorphous forms. This avenue should thus present the possibility of tuning stability to yield the right balance between bioavailability and shelf-life of the drug.

The non-crystalline state is also of interest as providing an alternative kinetic pathway to novel crystalline polymorphs. A dramatic recent example of this is the discovery of a previously unknown polymorph of ibuprofen, one of the most heavily studied pharmaceutical molecules, using a novel pathway that included the amorphous state.

The ability to characterize the solid-state structures of the drug is crucial to ensure the safety and therapeutic effect of the drug. The traditional method of choice for identifying (fingerprinting) polymorphs, and characterizing their structure quantitatively, is x-ray powder diffraction (XRPD). XRPD patterns are routinely placed in drug patents to uniquely identify the structural form (or forms) that will be approved for use as a commercial drug. Though single crystal studies are preferred for structure solution, quantitative analysis of XRPD patterns also can yield the atomic arrangement and molecular packing in the polymorphs (1), and is often the method of choice for refining previously solved structures using the Rietveld method (2, 3). In cases when single crystals are not available, or when studying powdered samples, such as phase analysis of a pellet, XRPD must be used and is highly successful. XRPD is therefore indispensable both in the pharmaceutical research and industrial communities.

A significant limitation of traditional crystallographic methods is that they break down on the nanoscale and are not appropriate for the characterization, or identification, of different a-phases and certain n-phases of drugs. Currently, there is no reliable experimental method for structural identification and characterization of amorphous and certain nanocrystalline pharmaceutical molecular solids. The powerful tools of crystallography begin to lose their power for structures on the nanoscale, sometimes referred to as the nanostructure problem (4). Conventional XRPD patterns become broad and featureless in these cases and are not useful for differentiating between different local molecular packing arrangements. These patterns can neither be used for identification of the structural phases present, other than a generic description that the structure is "amorphous" or "x-ray amorphous", nor can they be used for a full quantitative structural characterization (20). It has recently been suggested that Fourier transforming the conventional XRPD data to obtain a pair distribution function (PDF) (5, 6) allows more information to be extracted (7); however, there are no clear examples where this has successfully been applied to obtain a full quantitative structural characterization. The reason is that the information content in conventional XRPD data from "x-ray amorphous" samples is very limited, and PDF, which involves Fourier transformation of the data, does not add any information, and so the information content in the PDF is similarly limited.

Thus, atomic structures of certain nanostructured materials or amorphous pharmaceutical materials are not accessible by conventional methods used on crystalline materials. Furthermore, certain crystalline pharmaceutical materials with significant nano-range structural distortions which are not reflected in the average structure cannot be studied using conventional XRPD methods either. Thus, there is an important unsolved problem in nanoscience and in pharmaceutical characterization of certain non-crystalline forms, such as n-forms and a-forms, of drugs. Accordingly, there is a great need to characterize structures of solid small organic compounds, particularly pharmaceutical compounds.

SUMMARY OF THE INVENTION

One embodiment of the present invention is a method of characterizing a solid small molecule organic material. This method comprises subjecting the solid small molecule organic material to x-ray total scattering analysis. Data generated thereby may be collected, and the collected data may be transformed to provide a refined data set.

Another embodiment of the present invention is a product. This product comprises a data set of x-ray total scattering analysis of a solid small molecule organic material.

Yet another embodiment of the present invention is a method of comparing solid small molecule organic materials. This method comprises (a) subjecting a first solid small molecule organic material to x-ray total scattering analysis and collecting a first set of data generated thereby; (b) subjecting a second solid small molecule organic material to x-ray total scattering analysis and collecting a second set of data generated thereby; (c) optionally, mathematically transforming the first set of generated data to provide a first refined set of data and mathematically transforming the second set of generated data to provide a second refined set of data; and (d) comparing the first set of generated data and the second set of generated data or the first set of refined data and the second set of refined data to determine a difference or a similarity therein, wherein a similarity represents that the first and the second solid small molecule organic material have similar structures, and a difference represents that the first and the second solid small molecule organic material have different structures.

A further embodiment of the present invention is a method of characterizing a nanocrystalline solid small molecule organic material. This method comprises (a) subjecting the nanocrystalline solid small molecule organic material to x-ray total scattering analysis and collecting a first set of data generated thereby; (b) subjecting a crystalline solid small molecule organic material to x-ray total scattering analysis and collecting a second set of data generated thereby, wherein the crystalline solid small molecule organic material has the same molecular structure as the nanocrystalline solid small molecule organic material; and (c) applying a mathematical modulation to the first set of generated data, or the second set of generated data, or both the first set and the second set of generated data to determine the structure of the nanocrystalline material.

An additional embodiment of the present invention is an improved method of submitting to a regulatory agency data concerning the physicochemical properties of a drug or a drug product in the form of a small molecule organic material. In this method, the improvement comprises submitting x-ray total scattering information of the drug or the drug product.

Another embodiment of the present invention is a system for characterizing a solid small molecule organic material. This system comprises (a) an x-ray beam source device adapted to subject the solid small molecule organic material to a high frequency x-ray beam; (b) a detector coupled to the x-ray beam source device and adapted to collect total scattering data that result from diffraction of the high frequency x-ray beam by the solid small molecule organic material; and (c) a processor coupled to the detector and adapted to mathematically transform data generated by subjecting the solid small molecule organic material to the high frequency x-ray beam to provide a refined data set.

DETAILED DESCRIPTION OF THE INVENTION

Figure 1:
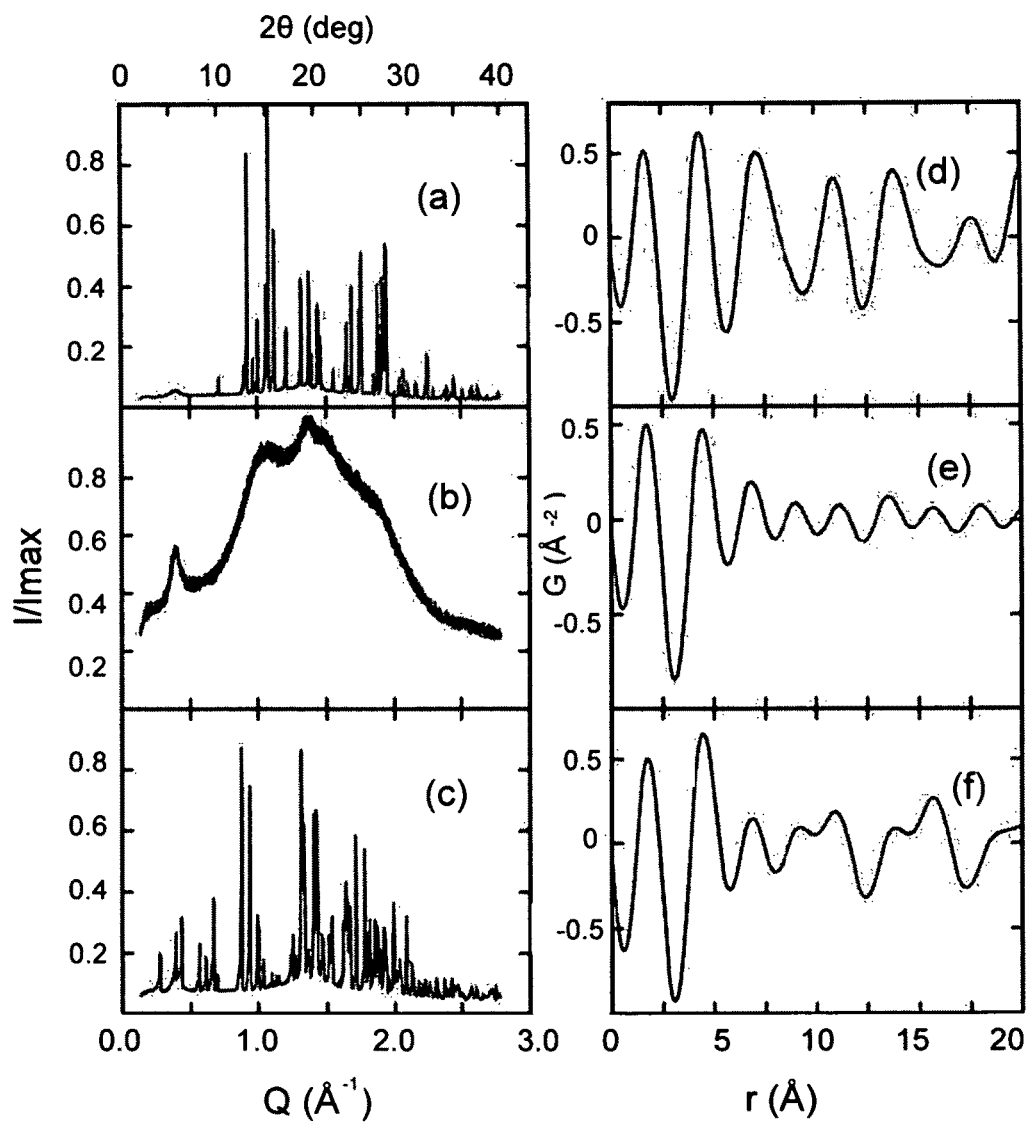
FIG. 1 compares data collected from different x-ray analysis of different forms of carbamazepine (CBZ). The top row of panels, (FIGS. 1(a), 1(d), 1(g), and 1(j)) contain pattern's from CBZ in the beta crystalline form, the middle row (FIGS. 1(b), 1(e), 1(h), and 1(k)) in the non-crystalline form, and the bottom row (FIGS. 1(c), 1(f), 1(i), and 1(l)) in the gamma crystalline form. The columns indicate data measured and analyzed in different ways. The first column (FIGS. 1(a), 1(b), and 1(c)) contains data from a Cu $K_\alpha$ x-ray source. The second column (FIGS. 1(d), 1(e), and 1(f)) contains the pair distribution functions (PDFs) obtained by Fourier transforming the conventional data shown in the first column. The third column (FIGS. 1(g), 1(h), and 1(i)) shows the synchrotron total scattering data in the form of F(Q). The fourth column (FIGS. 1(j), 1(k), and 1(l)) contains the total scattering data in the form of the total scattering PDF, G(r), obtained by Fourier transforming the data in the third column. The non-crystalline sample can be identified as being "amorphous" from the conventional XRPD data in the first two columns; however, the nature of the local packing cannot be ascertained. In contrast, in the third and fourth columns, it is immediately apparent that the non-crystalline sample resembles the β-form and not the γ-form.
Figure 1:
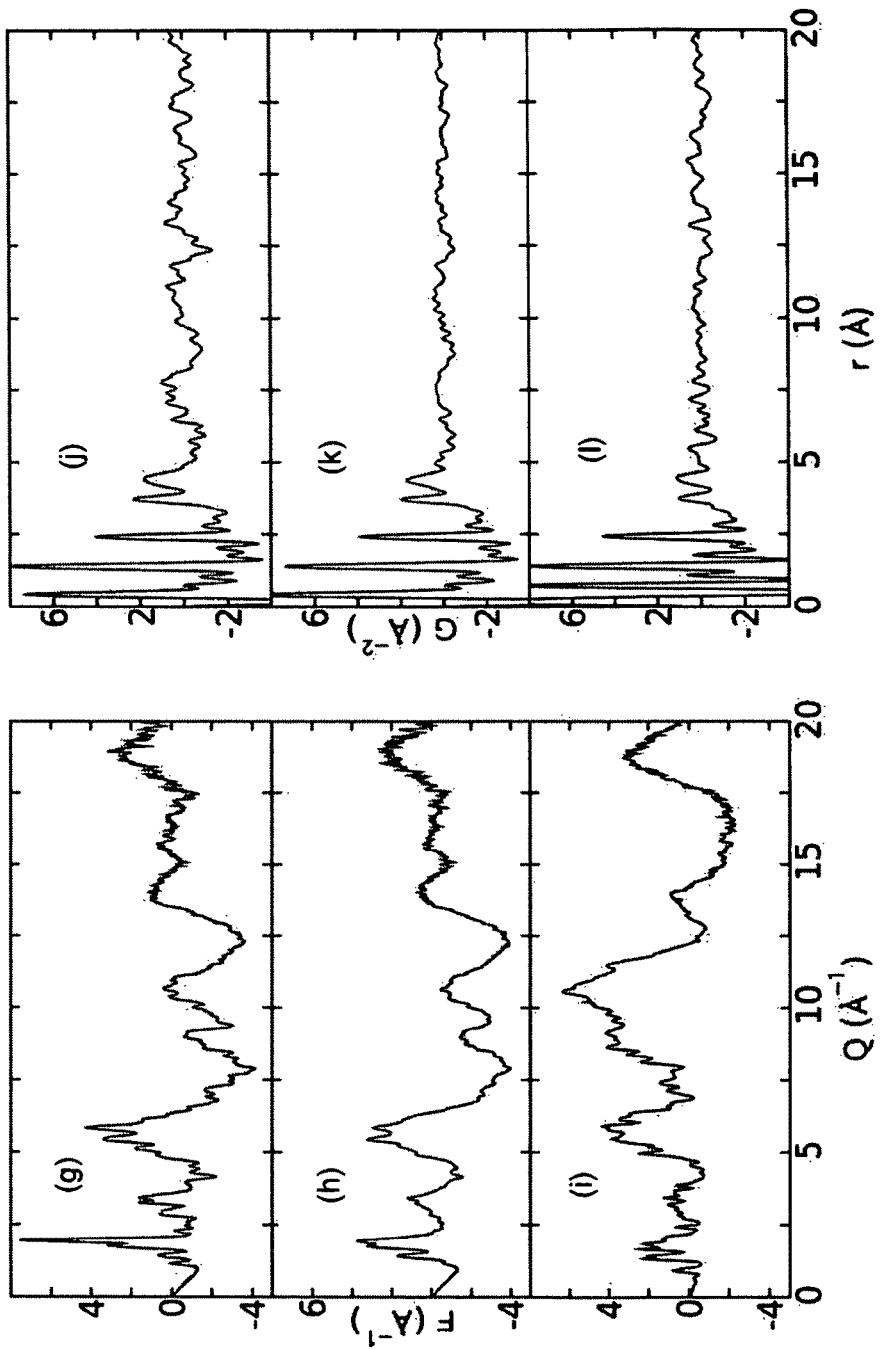

In accordance with the present invention, high-energy x-ray total scattering coupled with mathematical transformation of the generated data, such as making corrections to obtain the total scattering reduced structure function, F(Q), and pair distribution function analysis, produces unique structural fingerprints from amorphous and certain nano-structured phases of active pharmaceuticals. This new way of characterizing such materials opens the door to the quantitative study and application of drugs in these forms.

The present invention can be successful at both identifying the structural phase of amorphous and nanocrystalline forms of molecular solids, and also determining quantitative structural and molecular packing information from these materials. The results are surprising and unexpected. This approach yields unprecedented quality information that will be useful both in industrial and research settings in the study and commercialization of amorphous and nanocrystalline drugs and other molecular solids.

One embodiment of the present invention is a method of characterizing a solid small molecule organic material. This method comprises subjecting the solid small molecule organic material to x-ray total scattering analysis. Data generated thereby may be collected, and the collected data may be transformed to provide a refined data set.

As used herein, "X-ray total scattering analysis" means using high energy x-ray powder diffraction to provide structure-relevant scattering data over a wide range of reciprocal space, including both Bragg scattering and diffuse scattering. Bragg scattering means the set of sharp, discrete diffraction peaks exhibited by an ordered crystalline structure when bombarded with energy sources such as x-rays. When the structure is not completely ordered, then Bragg scattering intensities are diminished, and diffuse scattering intensities, which are the scattered intensities located outside Bragg scattering intensities, appear.

As used herein, "wide range of reciprocal space" means reciprocal lattice vector, Q, of at least above about 8.5 inverse angstroms. For example, Q may be above about 10, 12, 14, 16, 18, 20, 22, 24, 26, 28, or 30 inverse angstroms. For example, Q may be as low as about 0 inverse angstrom. Preferably, Q is from about 1 inverse angstrom to about 30 inverse angstroms, including from about 1 inverse angstrom to about 28 inverse angstroms, including from about 1 inverse angstrom to about 26 inverse angstroms, including from about 1 inverse angstrom to about 24 inverse angstroms, including from about 1 inverse angstrom to about 22 inverse angstroms, including from about 1 inverse angstrom to about 20 inverse angstroms, about 1 inverse angstrom to about 18 inverse angstroms, and from about 1 inverse angstrom to about 16 inverse angstroms, including from about 1 inverse angstrom to about 14 inverse angstroms, including from about 1 inverse angstrom to about 12 inverse angstroms, and including from about 1 inverse angstrom to about 10 inverse angstroms. Q values are determined using the following equation:

$$Q = \frac{4\pi \sin(\theta)}{\lambda},$$

wherein $\theta$ is the Bragg angle, and $\lambda$ is the wavelength of the x-ray beam. As used herein, a "Bragg angle" means half scattering angle, which is the angle between the beam axis and the scattered intensity.

"High energy x-ray powder diffraction" means x-ray powder diffraction carried out using high frequency x-ray beams, the wavelength of which is less than or equal to 1.1 angstroms. For example, high energy x-ray powder diffraction may be carried out using x-ray beams, the wavelength of which is less than or equal to 0.8 angstroms. Preferably, the x-ray source is synchrotron radiation. The key, however, is not the use of synchrotron radiation per se but collecting data over a wide range of Q with good statistics. It is understood by those skilled in the art that such data is obtainable from many difference x-ray beam sources other than synchrotron radiation, such as laboratory based diffractometers that have silver or molybdenum sources (13). Instruments with a molybdenum source are commercially available from such manufactures as Siemans Corporation (New York, N.Y.) and General Electric (Fairfield, Conn.). The data presented in the Examples below were Fourier transformed with a $Q_{max}$ of 18Å$^{-1}$, which is accessible with a silver source lab diffractometer. Such instruments are currently under development by Panalytical B.V. (Almelo, the Netherlands) and Bruker Bio-Spin Corp. (Billerica, Mass.). The synchrotron measurements are preferable because the requisite statistics can be obtained over the whole Q-range in a short time (approximately 30 minutes) compared to many hours on a lab-based source. Future developments in high intensity laboratory sources with silver anodes could help this situation considerably.

The term "solid" means states of matter characterized by resistance to deformation and changes of volume. A "small molecule organic material" means any chemical compound, or a salt, a solvate, or a hydrate thereof, which contains one or more carbon atom(s) and the individual molecules of which are no more than 3 nm in length. In a preferred embodiment, the individual molecules of the small molecule organic material are no more than 2 nm in length, and more preferably, less than 1 nm in length. In another preferred embodiment, the small molecule organic material contains one or more carbon atom(s) and at least one other element, such as hydrogen, nitrogen, and/or oxygen. For example, the carbamazepine molecule contains carbon, hydrogen, nitrogen, and oxygen, and the indomethacin molecule contains a chlorine in addition to carbon, hydrogen, nitrogen, and oxygen. In yet another preferred embodiment, the small molecule organic material contains carbon, hydrogen, and at least one additional element. In an additional preferred embodiment, the small molecule organic material contains carbon, hydrogen, and nitrogen; or carbon, hydrogen, and oxygen. In yet another preferred embodiment, the small molecule organic material is a drug or a drug product.

As used herein, the term "drug" means (A) articles recognized in the official United States Pharmacopoeia, official Homoeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals; and (D) articles intended for use as a component of any article specified in clause (A), (B), or (C).

The term "drug product" means any article that contains any drug. Drug product includes pure chemical entity or any composition, mixture or formulation containing the drug product. For purposes of characterization, identification, and/ or comparison, the drug product is in the form of purified small solid organic molecule of interest.

The solid small molecule organic material that is subjected to x-ray total scattering analysis is in the form of a powder, preferably a fine powder, or any other form that scatters isotropically, or almost isotropically, such as an amorphous or nanocrystalline solid. Such sample may be prepared in any methods that are suitable for samples used in conventional x-ray powder diffraction. The samples may be placed in a capillary, on a plate, or any other platforms or containers or other means as directed by the manufacturer of the x-ray powder diffraction instrument.

In one aspect of this embodiment, the method further comprises collecting data generated by x-ray total scattering analysis of a solid small molecule organic material, and mathematically transforming the generated data to provide a refined data set.

Collecting data generated by x-ray total scattering analysis of a solid small molecule organic material includes, but is not limited to gathering, displaying, and/or recording relevant structural x-ray data, e.g., over a range of Bragg angles. For example, data that may be generated and collected include an associated intensity of the diffraction at a specific Bragg angle, wavelength of the x-ray beam, position of the detector used to record the intensity of the diffraction and the associated intensity of the diffraction at a specific position, and/or total scattering data. The generated data may be recorded, captured, displayed, and/or saved in any convenient manners, for example, on film or by a machine such as a computer.

As used herein, "mathematically transforming" the generated data to provide a refined data set means manipulating data mathematically such that the pre-transformed data, e.g., generated data, is related to the post-transformed data, e.g., the refined data set, by a specific function. For example, pre-transformed data may be divided, subtracted from, or otherwise normalized by any smoothing function whose periodicity is greater than $2\pi/d$, wherein d is the nearest neighbor distance, which is the smallest distance between two atoms in the material. Smoothing function means any function which has continuous derivative over the range and around which the pre-transformed data oscillates. An example is a portion of a Gaussian distribution that fits within the pre-transformed data. Other examples are provided below. Mathematical transformations also include Fourier transformation, which is an operation that transforms one complex-valued function of a real variable into another. Mathematical transformations are preferably performed by a machine, such as a computer, using programs, such as PDFgetX2 (16). However, it is understood by those skilled in the art that other comparable programs may be used to perform mathematical transformations. Such comparable programs include RAD, FIT, PEDX, and IFO (17-19).

In one preferred embodiment, the generated data are mathematically transformed to a reduced total scattering structure function. As used herein, "reduced total scattering structure function," F(Q), is obtained by the following equation:

$$F(Q)=Q[S(Q)-1]$$

where S(Q), the total scattering structure function, contains the measured intensity from the small molecule organic material and is defined in the equation as follows:

$$S(Q) = \frac{I_c(Q) - \langle f^2 \rangle}{\langle f \rangle^2} + 1$$

wherein $I_c(Q)$ is the powder diffraction intensity that may or may not have been corrected according to experimental conditions, and wherein f=Z is the atomic scattering factor evaluated at Q=0, where Z is the atomic number. Preferably, $I_c(Q)$ is the powder diffraction intensity that has been properly corrected by removing experimental artifacts, fluorescence, multiple scattering and Compton scattering, corrected for such effects as sample self-absorption, and normalized by the incident intensity and the number of scatterers in the sample. The notation, < . . . >, indicate compositionally weighted averages over the atomic species in the sample. Another way of writing the equation deriving S(Q) is as follows:

$$S(Q) = \frac{I_c(Q) - \sum c_i |f_i(Q)|^2}{|\sum c_i f_i(Q)|^2} + 1,$$

Wherein $c_i$ and $f_i$ are the atomic concentration and x-ray atomic form factor, respectively, for the atomic species of type i, and $\Sigma c_i=1$.

In another preferred embodiment, the generated data are mathematically transformed to an experimentally derived atomic pair distribution function (PDF). "Experimentally derived atomic pair distribution function (PDF)" is related to the measured total scattering data through a sine Fourier transform. The general sine Fourier transform function is as follows:

$$G'(r) = 2c \int_x^y F(Q)\sin(Qr)\,dQ$$

where r is a radial distance, and c is any constant, and x is greater than or equal to 0; and y is any number between 0 and infinity.

It is understood by those skilled in the art that the equations set forth above may be re-written in a different way depending on the experimental conditions, such as corrections for background and/or anomalous-scatterings. For example, the PDF may be linked the scattering through the sine Fourier transform:

$$G(r) = (2/\pi) \int_{Q_{min}}^{\infty} F(Q)\sin(Qr)\,dQ$$

wherein $Q_{min}$ is a Q value that excludes any small angle scattering intensity but includes all the wide-angle scattering (10).

In another aspect of this embodiment, the solid small molecule organic material is a crystalline material. In a further aspect of this embodiment, the solid small molecule organic material is a non-crystalline material. Preferably, the non-crystalline material is a nanocrystalline material or an amorphous material. In an additional aspect of this embodiment, the solid small molecule organic material is a distorted material.

As used herein, a "crystalline material" means any material that have long-range order. Its structure may be defined by a small number of parameters that define the unit cell (its shape and size) and its contents (atomic coordinates and thermal factors). The complete structure is then obtained by periodically repeating this unit cell over the long range, which means a range of greater than about 100 nm. Crystalline materials include those materials that have a crystal structure but with a different structure on the nanoscale.

A "distorted material" means a material with long-range order, but has significant structural distortions, which are not reflected in the average structure.

A "non-crystalline material" is any material that is not a crystalline material nor a distorted material. A non-crystalline material includes but is not limited to amorphous material and nanocrystalline material.

An "amorphous material" means a material that does not have well-defined structure or has well-defined structure under about 10 angstroms.

A "nanocrystalline material" means a material that has well-defined structure over local and intermediate ranges of about 10 angstroms to about 1000 angstroms. For example, a nanocrystalline material may have well-defined structure over the range of about 10-800 angstroms, including about 10-700 angstroms, 10-600 angstroms, 10-500 angstroms, 10-400 angstroms, 10-300 angstroms, 10-200 angstrom, 10-150 angstroms, and about 10-100 angstroms. It can often be described by a small unit cell and a small number of parameters, but the order extends only on a nanometer length-scale. Note that this definition of nanocrystals goes beyond perfect crystals that are simply very small (nanometer in size) and includes material where the particle size can be larger but the structural coherence is at the nanometer length-scale. Certain nanocrystalline material appears as "amorphous" if analyzed using conventional XRPD, or is "x-ray amorphous". Examples of such nanocrystalline materials are set forth in Examples 1-4 below.

A further embodiment of the present invention is a product. This product is made according to any of the methods disclosed above.

Another embodiment of the present invention is also a product. This product comprises a data set of x-ray total scattering analysis of a solid small molecule organic material. The solid small molecule organic material is as disclosed above.

Yet another embodiment of the present invention is a method of comparing solid small molecule organic materials. This method comprises (a) subjecting a first solid small molecule organic material to x-ray total scattering analysis and collecting a first set of data generated thereby; (b) subjecting a second solid small molecule organic material to x-ray total scattering analysis and collecting a second set of data generated thereby; (c) optionally, mathematically transforming the first set of generated data to provide a first refined set of data and mathematically transforming the second set of generated data to provide a second refined set of data; and (d) comparing the first set of generated data and the second set of generated data or the first set of refined data and the second set of refined data to determine a difference or a similarity therein, wherein a similarity represents that the first and the second solid small molecule organic material have similar structures, and a difference represents that the first and the second solid small molecule organic material have different structures.

In one aspect of this embodiment, the method comprises mathematically transforming the first set of generated data to provide a first refined set of data and mathematically transforming the second set of generated data to provide a second refined set of data.

In one preferred embodiment, the first set of generated data and the second set of generated data are mathematically transformed to a reduced total scattering structure function. In another preferred embodiment, the first set of generated data and the second set of generated data are mathematically transformed to an experimentally derived atomic pair distribution function (PDF). Reduced total scattering structure function and experimentally derived atomic pair distribution function are as disclosed above.

Comparing two or more sets of data or graphical representation of the data may be performed in any convenient way. Comparisons may be performed manually. Preferably, comparisons are performed using a machine, such as a computer. Data may be presented in reciprocal space or in real space. All sets of data may be presented in a graphical manner, with the independent variable on the x-axis and the dependent variable on the y-axis. For example, data may be presented as a plot of 2θ vs. intensity, θ vs. intensity, Q vs. intensity, Q vs. F(Q), and r vs. G(r). Preferably, data are presented as a plot of Q vs. F(Q), or r vs. G(r). The variables, θ, Q, F(Q), r, and G(r) are as defined above.

Data may be compared using qualitative methods. For example, two or more sets of data may be superimposed on each other for the ease of comparing the position and height of features (such as peaks and valleys) in the plot.

Data may also be compared quantitatively. Many statistical tests suitable for comparing two sets or more sets of data are available. For example, a "goodness of agreement" parameter between the two sets of data may be specified. Such a parameter may be accomplished by evaluating the sum of difference over a range of the data points defined as $\Sigma(P_i(1)-P_i(2))$, where $P_i(1)$ is the value of the $i^{th}$ point in the first set of data, and $P_i(2)$ is the value of the $i^{th}$ pointing in the second set of data. In other words, one set of data is designated as the reference. At each point of the independent variable, the dependent variable of the reference is subtracted from the corresponding dependent variable of the other set of data. The result of the subtraction is the difference between a set of data and the reference data. The result of the subtraction may further be presented in a graphical manner, with the independent variable on the x-axis and the dependent variable being the result of the subtraction.

Furthermore, a "goodness of agreement" parameter may be accomplished by evaluating the sum of mean-square difference over a range of the data points defined as $\Sigma(P_i^2(1)-P_i^2(2))$ or by evaluating the sum of the difference squared over a range of the data points defined as $\Sigma(P_i(1)-P_i(2))^2$, where $P_i(1)$ is the value of the $i^{th}$ point in the first set of data, and $P_i(2)$ is the value of the $i^{th}$ pointing in the second set of data. It is understood by those skilled in the art that there are a number of similar expressions that may be used to accomplish the same purpose. For example, each point in the sum could be weighted by a measure of its statistical significance, or the evaluation could be carried out after any low-frequency backgrounds have been removed from the data by fitting and subtraction.

Another example of a quantitative method is based on an evaluation of a number of strongest peaks. Here, peaks refers to the high points in a graph when the data is presented in a graphical format, or the corresponding points of data when not presented in a graphical format. "Strongest peaks" refers to those peaks with the biggest amplitudes. In this method, the position and the amplitude of the strongest 1-30 peaks in the first set of generated data or in the first set of refined data are determined. Preferably, the strongest 5-15, and more preferably, the strongest 10 peaks are determined. These peaks are compared to the corresponding number of strongest peaks in the second set of generated data or refined data. Optionally, the amplitude of the intensities or peaks in both sets of data are normalized, for instance, by scaling to the amplitude of the strongest peak.

The judgment whether the two sets of data are similar or different depends on the evaluation of the position and the amplitude of the peaks. The judgment may be made solely on the basis of the position of the peaks. For example, the two sets of data may be judged to be the same if the positions of the peaks or the intensities differ no more than 30% of total range of data examined, including not more than 20%, 10%, 5%, 1%, 0.5%, 0.1%, 0.05%, or 0.01% of the total range of the data examined. The judgment may also be made solely on the basis of the amplitudes of the peaks. For example, the two sets of data may be judged to be the same if the amplitudes of the peaks from the second set of data are within 30%, preferably within 20%, or within 10% of the amplitude of the corresponding peaks from the first set of data. Preferably, the judgment whether the two sets of data are similar or different depends both the positions and the amplitudes of the peaks.

Other statistical methods, such as correlation measurements, may also be used to analyze the differences and similarities between two or more sets of data. Correlation analysis includes, for example, Pearson correlation, Kendall rank correlation and Spearman correlation. Generally, correlation analysis gives a correlation value R in the range of −1 to 1 between each pair of data-set. A value of 1 implies complete correlation, zero means uncorrelated, and a value of −1 implies complete inverse correlation. If two sets of data are highly correlated, then they are highly similar. If two sets of data are uncorrelated, then they are highly dissimilar. Correlation techniques are extremely powerful because they ignore absolute scaling, but are sensitive to relative scaling and slight shifts in peak positions.

Additionally, commercial computer software programs are available to analyze the differences and similarities between two or more sets of data. For example, PolySNAP2 and PolySNAP M (University of Glasgow, Glasgow, United Kingdom) rank patterns in order of their similarity to any selected sample (25). These software programs give a number between 0 and 1 to describe the similarity or differences, with 0 signifying that two sets of data are very different, and 1 signifying that the two sets of data are the same. IBM SPSS Statistics software (SPSS Inc., Chicago, Ill.) may also be used to provide correlation coefficients using Pearson correlation, Kendall rank correlation and/or Spearman correlation methods.

Comparison may be performed over a range of points, such as the entire data set, or 10%, 20%, 30%, 40%, 50%, 60%, 70%, 80%, 90%, 91%, 92%, 93%, 94%, 95%, 96%, 97%, 98%, or 99% of the data set. It may also be performed over data corresponding to the range dominated by inter-molecular interactions, such as above 3 angstroms, including 3-20 angstroms or 3-30 angstroms. Larger range, for example, from 0.1-30 angstroms, may also be used. Preferably, the entire data set is used. The range may be continuous, or discontinuous.

In an additional aspect of this embodiment, mathematical transformation of at least one set of generated data comprises scaling, stretching, smearing, or a combination thereof. The scaled, stretch, or smeared data may then be compared to the other set of transformed data.

"Scaling" means to multiply the data by a multiplier, or a scale factor. The scale factor may be a constant. Scaling may be performed manually or automatically using a computer program. For example, when manually scaling the one set of data, the data points are multiplied a given scale factor.

Automatically scaling one set of data to the other set may be done in many ways. One way is to determine the scale factor via linear regression with zero offset. In this procedure, the scale factor is determined according to the standard linear regression formula: the covariance of the first and second data sets divided by the variance of the first data set.

Another example of a scaling method uses physical considerations to scale the first data set, which is preferably transformed to PDF first. In this procedure, the PDF is converted to the radial distribution function (RDF) by subtracting a linear baseline from the PDF and multiplying this by r, the radial distance. This baseline is either provided manually or estimate by fitting the bottom of the low-r signal with a linear function via least-squares regression. The estimated baseline may be pre-set to prefer the bottom of the low-r signal by adding a penalty function to the least-squares cost function where the estimated baseline is greater than the low-r signal. The RDF is obtained from the PDF by subtracting this baseline and multiplying the result by r. This operation may be performed for both sets of data. The RDF represents the weighted average number of atom-pairs within a given interaction distance, and its integral is the weighted total number of atom pairs within a given interaction distance. To scale the first set of data in the form of RDF, it is divided by its integral and multiplied by the integral of the other RDF. This procedure therefore scales the first set of data in the form of RDF to represent the same number of atom pairs as the second set of data in the form of RDF. Once the first set of data in the form of RDF is scaled, the baseline is also scaled. Subsequently, the data in the form of RDF is converted back into the PDF. This method requires a good baseline estimate for both sets of data. Thus, to use this method, data are usually collected from macroscopic samples, because nano-scale samples may not have a linear baseline.

Figure 6:
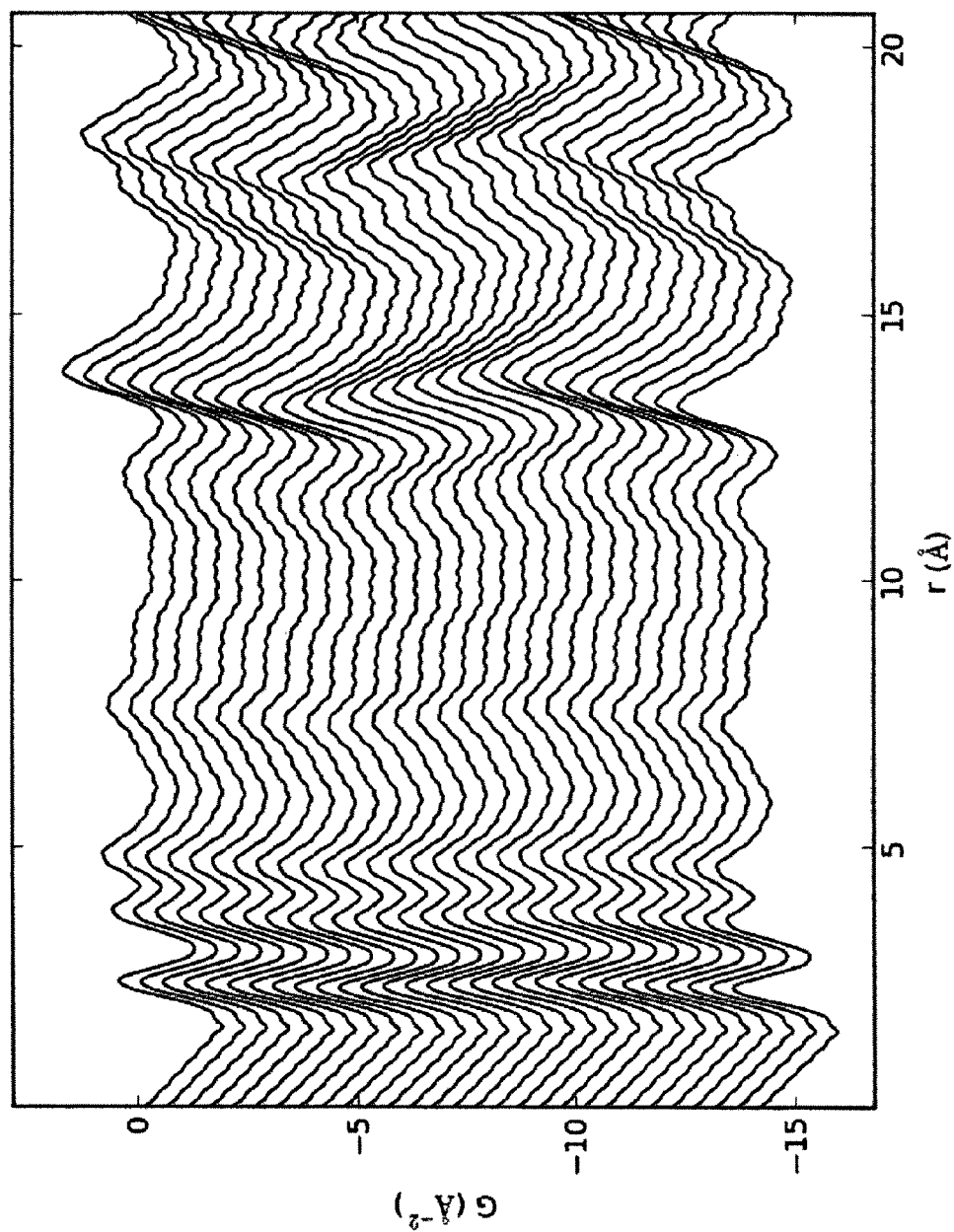
FIG. 6 shows data collected from aspirin in the form of PDF being stretched.

"Stretching" means extending or compressing the data, preferably in the form of PDF, on the r-scale, like a concertina, to mimic changes in lattice parameter. FIG. 6 shows a PDF of aspirin being stretched. Stretching may be used to simulate a difference in temperature at which the samples were subjected to x-ray total scattering analysis, for example. Stretching one set of data in the form of PDF onto the other may be performed by rescaling the r-axis of the first set of data. Given a stretch factor, the r-values are multiplied by (1+stretch factor) to expand or contract the r-scale by the desired amount. The stretched data are then linearly interpolated (re-binned) back onto its original grid from the stretched grid for easier comparison with the other set of data in the form of PDF. The stretch factor may be determined manually, by trial and error, for example. When automating this operation, the scale factor is determined via least-squares regression, where the absolute difference between the two sets of data is minimized. This operation may be performed on the data in the PDF form or on the data using an estimated RDF, as described above.

Figure 5:
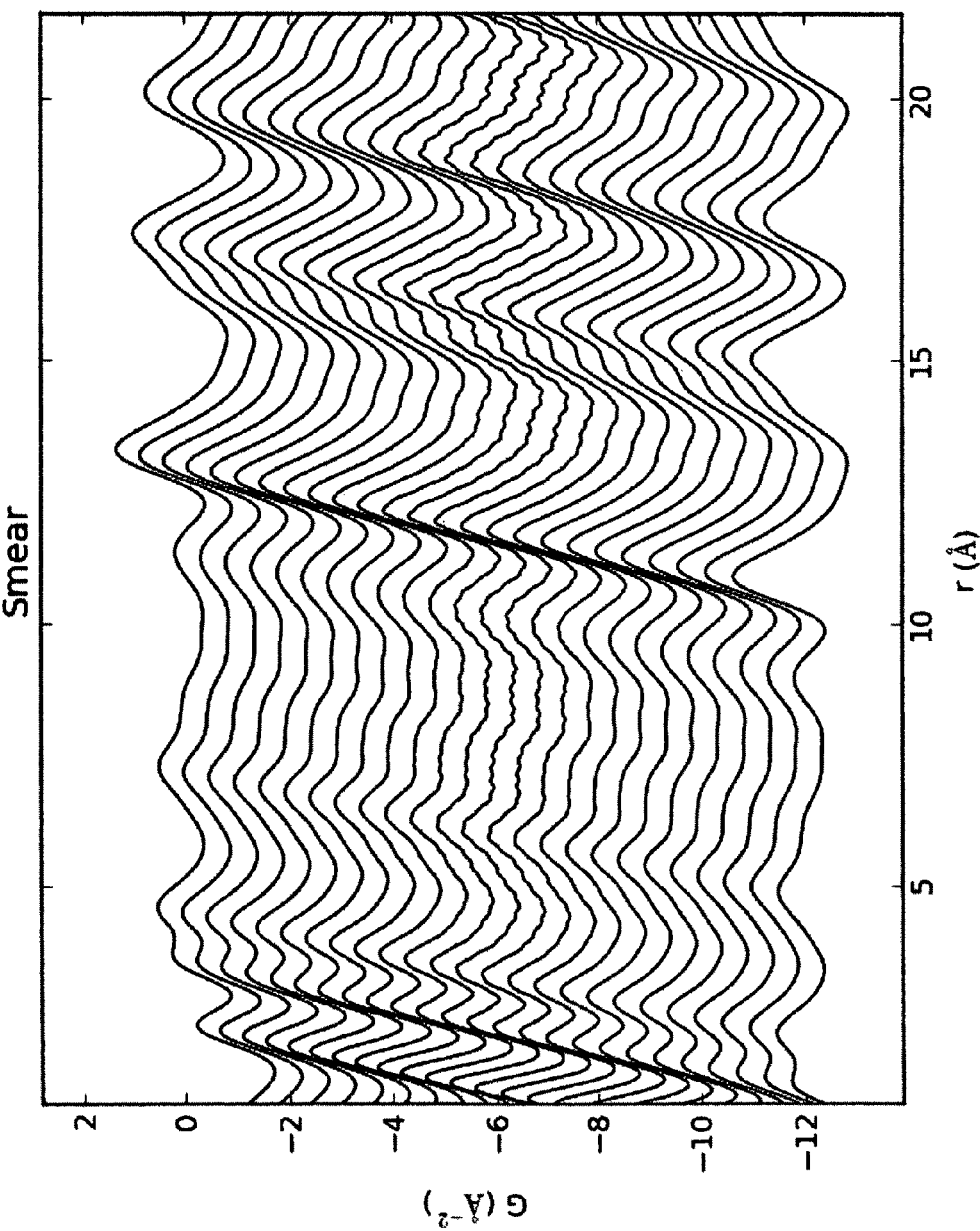
FIG. 5 shows data collected from aspirin in the form of PDF being smeared.

"Smearing" means broadening of certain features in one set of data, preferably in the form of PDF, to simulate peak broadening in the second set of data, preferably also in the form of PDF. Such broadening may be used to simulate a difference in temperature at which the samples were subjected to x-ray total scattering analysis, for example. FIG. 5 shows a PDF of aspirin being smeared. Preferably, smearing is performed on data in the form of an estimated RDF rather than the PDF, because the RDF peaks are Gaussian whereas the PDF peaks are not (though the errors are quite small if data in the form of PDF is smeared directly). Preferably, to perform the smear operation, the PDF is converted to the RDF as described above, and then the data are convoluted with a Gaussian with a chosen broadening factor as the width. The numerical convolution is performed such that the centroid and integrated amplitude of the smeared data does not change. Smearing may be performed automatically, for example, via least-squares regression as described above.

In sum, scaling, stretching and smearing may be automated using a regression algorithm (e.g., least squares) so that the optimal values for the scale, stretch and smear factors are found such that they morph one set of data, preferably in the form of PDF or RDF, as close as possible to the second set of data, also preferably in PDF or RDF. Note that these operations may be combined. For example, during each regression loop, one set of data may be scaled, stretched and smeared in that order (or in another order) as described above, according to parameters provided by the optimization algorithm. Preferably, the conversion from PDF to RDF is performed once, before regression, and the conversion from RDF to PDF is performed as described above after the optimal morphing parameters are found.

In another aspect of this embodiment, the first solid small molecule organic material and the second solid small molecule organic material have the same molecular structure, but have been subjected to different processing protocol. As used herein, different processing protocol means being treated under different conditions, such as temperature, pressure, and/or chemical environment. For example, the second small molecule organic material may be a recrystallized form of the first small molecule organic material. Recrystallization process may include a different temperature annealing regimen or a different solvent system, for example. Preferably, different processing protocol is different storage times and/or storage conditions. More preferably, the method further comprises correlating the differences in the first set of generated data and the second set of generated data or the differences in the first set of refined data and the second set of refined data, the storage time, or the storage condition to the stability of the solid small molecule organic material.

As used herein, "molecular structure" means three-dimensional arrangement of the atoms that constitute a molecule, but does not include the three-dimensional arrangement of the molecules into a larger structure. "Storage time" means duration from the time the solid small molecule organic material is made to the time the x-ray total scattering data from the small molecule organic material is collected. "Storage condition" means the condition under which the solid small molecule organic material is stored after it was made. Storage condition includes but is not limited to temperature, pressure, pH, humidity, and light, chemical composition of the atmosphere or combinations thereof. As used herein, "chemical composition of the atmosphere" means the gaseous substance(s) (if any) with which the sold small molecule organic material is in contact. Some non-limiting exemplary chemical composition of the atmosphere include vacuum, pure nitrogen, and composition of air at sea level.

As used herein, "correlating" means relating. The relationship may or may not be linear. Such correlation yields different information regarding a solid small molecule organic material, including stability information and consistency of manufacturing process.

For example, to assess the stability of a solid small molecule organic material over a certain period of time, a sample of the material may be subjected to x-ray total scattering analysis. After a certain period of time, a second sample of the material may be subjected to x-ray total scattering analysis. If it is determined that the two sets of generated data or refined data are the same, then the sample is stable for that period of time. Conversely, if it is determined that the two sets of generated data or refined data are different, then the sample is degrading over that period of time. Methods of comparing the two sets of data are as set forth above.

In another example, the effects of different storage condition on the solid small molecule organic material may be assessed. Two different samples of the material may be stored under different temperatures, one at 20° C., and the other at 4° C. After a certain period of time, both samples may be subjected to x-ray total scattering analysis. If it is known that the material is stable at 4° C. over that period of time, and if it is determined that the two sets of generated data or refined data are the same, then the differences in temperature does not have an effect on the stability of the material. The material may also be stored at 20° C. over that period of time. Conversely, if it is determined that the two sets of generated data or refined data are different, then the differences in temperature have an effect. This example may be applied mutatis mutandis to other storage conditions such as light, humidity, pressure, pH, or combinations thereof.

In yet another example, x-ray total scattering analysis may also be used to verify the consistency of a manufacturing process for such a material. A sample may be taken from two different lots of a solid small molecule organic material, which were manufactured using the same synthetic process. Both samples may be subjected to x-ray total scattering analysis. If it is determined that the two sets of generated data or refined data are the same, then there is consistency in making the material. Conversely, if it is determined that the two sets of generated data or refined data are different, then the manufacturing process is inconsistent. This example may be applied mutatis mutandis to changes in manufacturing process, including without limitation, scaling up the production of a solid small molecule organic material, use of different solvent or machineries in the production process, change of starting material and synthetic scheme.

A further embodiment of the present invention is a method of characterizing a nanocrystalline solid small molecule organic material. This method comprises (a) subjecting the nanocrystalline solid small molecule organic material to x-ray total scattering analysis and collecting a first set of data generated thereby; (b) subjecting a crystalline solid small molecule organic material to x-ray total scattering analysis and collecting a second set of data generated thereby, wherein the crystalline solid small molecule organic material has the same molecular structure as the nanocrystalline solid small molecule organic material; and (c) applying a mathematical modulation to the first set of generated data, or the second set of generated data, or both the first set and the second set of generated data to determine the structure of the nanocrystalline material.

In one aspect of this embodiment, the mathematical modulation comprises mathematically transforming the first set of generated data and the second set of generated data using a PDF to provide a first set of refined data and a second set of refined data; and apply a mathematical function to the second set of refined data to generate a modified second set of data such that the modified second set of data is in substantial agreement with the first set of refined data; wherein the mathematical function mimics the loss of far neighbor contribution outside a hypothetical particle, and wherein the size of the hypothetical particle is the size of the nanocrystal. PDF is as disclosed above.

In one example, the hypothetical particle is spherical. The mathematical function mimicking the loss of far neighbor contribution outside a hypothetical spherical particle is as follows (11):

$$f(r; d) = \left[1 - \frac{3r}{2d} + \frac{1}{2}\left(\frac{r}{d}\right)^3\right]\Phi(d - r),$$

wherein d is the diameter of the spherical particle, and φ(x) is a Heaviside step function that has value 1 in the region r≤d and value 0 for r>d.

Substantial agreement may be determined by a qualitative method or a quantitative method which minimizes the differences between the modified second set of data and the first set of refined data. In one example, the differences between the modified second set of data and the first set of refined data may be described by the "goodness of agreement" parameters as set forth above in the disclosure relating to methods for comparing data. In another example, differences between the modified second set of data and the first set of refined data may be minimized using existing statistical softwares, such as PolySNAP 2 and PolySNAP M.

Furthermore, this method may be used to extract quantitative data, for example, about the percentage of crystallization in a sample known to start as a nanocrystalline material and over time, crystallize into a crystalline material. The starting material and degraded material may be first subjected to x-ray total scattering analysis, and mathematically transformed to provide a refined set of data. The sample is then subjected to x-ray total scattering analysis and mathematically transformed in a manner similar to the starting material and degraded material. Methods of mathematical transformation are as set forth above. The refined data from the starting material and the degraded material may be linearly combined, or modeled as set forth above, until substantial agreement is reached between the linearly combined data and the refined data of the sample, or between the modeled data and the refined data of the sample.

Another embodiment of the present invention is an improved method of submitting to a regulatory agency data concerning the physicochemical properties of a drug or a drug product in the form of a small molecule organic material. In this method, the improvement comprises submitting x-ray total scattering information of the drug or the drug product to the regulatory agency.

The term "regulatory agency" means a body that establishes, monitors, reforms or enforces standards in a specific area of activity. Regulatory agencies include, without limitation, United States Food and Drug Administration, European Medicines Agency, or any regulatory body which regulates drugs in the world.

The term "x-ray total scattering information" means data generated from x-ray total scattering analysis and any derivations thereof, including but not limited to mathematically transformed data such as PDF data, data from reduced total scattering structure function, graphical representations of such data, description of the data, and any conclusion drawn from the data.

In one aspect of this embodiment, the regulatory agency is the United States Food and Drug Administration (FDA).

In another aspect of this embodiment, the submission is made in an investigational new drug application, an application for FDA approval to market a new drug (NDA), an abbreviated new drug application (ANDA), or in relation to maintaining the identity or quality of the solid drug.

In an additional aspect of this embodiment, the submission is made in an application for approval of a drug in amorphous or nanocrystalline form. As used herein, an "approved drug" means a drug or a drug product that is approved for sale or marketing by a regulatory agency, including for example, the FDA. The amorphous or nanocrystalline form of the approved drug has the same molecular structure as the approved drug, but may differ in local arrangements and hence may be more bioavailable than the approved drug.

In a further aspect of this embodiment, the submission is made in compliance with a requirement of Code of Federal Regulations (CFR), specifically, 21 CFR 211, 21 CFR 312, or 21 CFR 314. It is understood that CFRs may change over time and that the specific sections of CFR cited herein include successor provisions.

For example, stability information gathered from x-ray total scattering analysis may be submitted to the FDA and for the purposes of complying with good manufacturing practice for finished pharmaceuticals, for example, the requirements of 21 CFR 312.23 (investigational new drug application), 21 CFR 314.50 (application for FDA approval to market a new drug), 21 CFR 211.137 (expiration dating), 211.166 (stability test), 211.170 (testing of reserved samples), and 211.194 (maintenance of laboratory records, including stability test results).

X-ray total scattering analysis may further be used in manufacturing process control and submitted to the FDA for the purposes of submitting an investigational new drug application, for example 21 CFR 312.23; for the purposes of application for FDA approval to market a new drug, for example, the requirements of 21 CFR 314.50(d)(1); and for the purposes of complying with good manufacturing practice for finished pharmaceuticals, for example, the requirements of 21 CFR 211.84, 211.110, 211.160, and 211.194.

Additionally, x-ray total scattering analysis may be submitted in compliance with the requirements of 21 CFR 314.53 for patents that claim a polymorph that is the same as the active ingredient described in the approved or pending application.

X-ray total scattering analysis may also be used by the generic manufacturer to the FDA in an ANDA, in compliance with the requirements 21 CFR 314.94. Among other information, 21 CFR 314.94 requires chemistry, manufacturing and control information, including requirements of 21 CFR 314.50(d)(1)(i).

Figure 4:
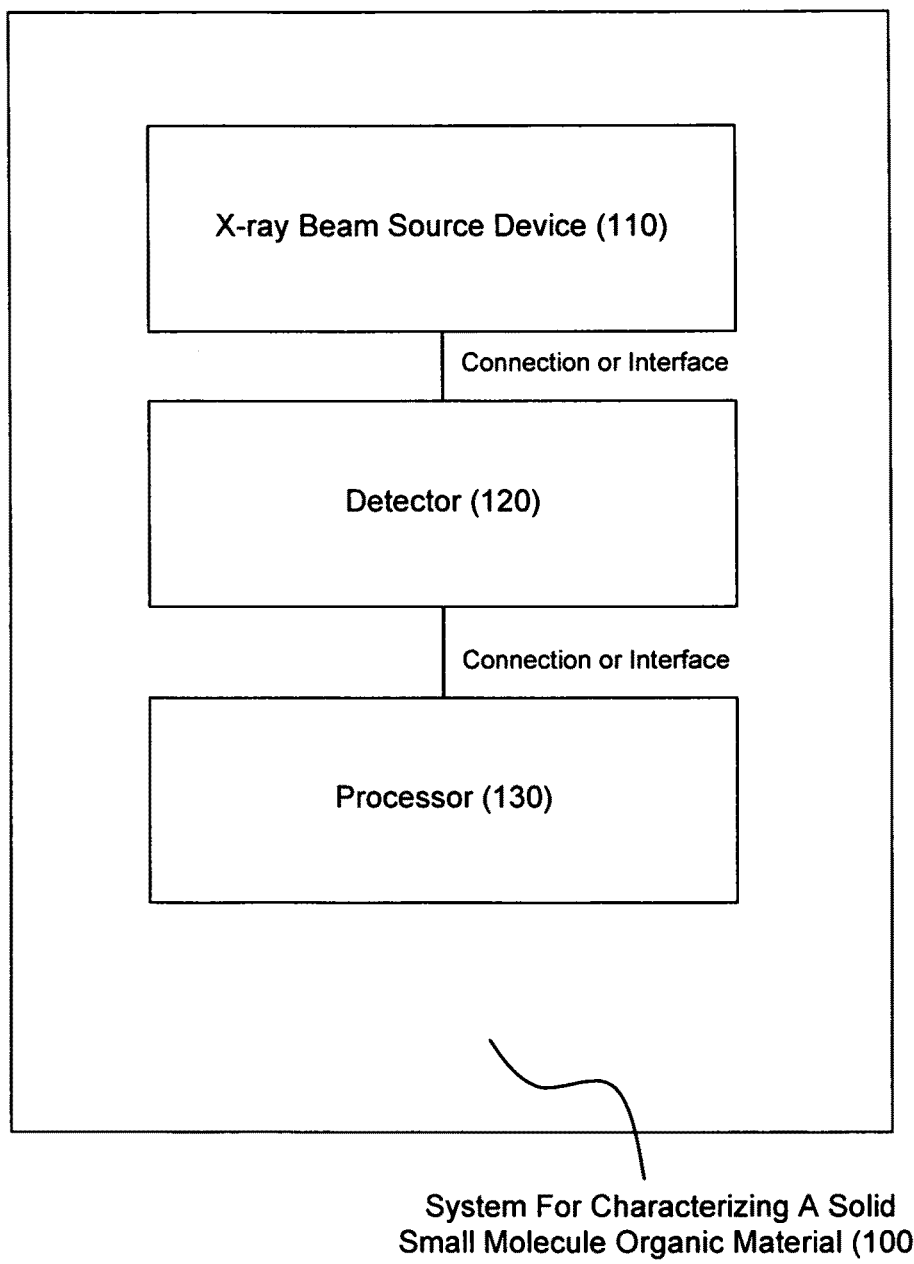
FIG. 4 is a schematic showing a system for characterizing a solid small molecule organic material.

Another embodiment of the present invention is a system for characterizing a solid small molecule organic material. This system comprises (a) an x-ray beam source device adapted to subject the solid small molecule organic material to a high frequency x-ray beam; (b) a detector coupled to the x-ray beam source device and adapted to collect total scattering data that result from diffraction of the high frequency x-ray beam by the solid small molecule organic material; and (c) a processor coupled to the detector and adapted to mathematically transform data generated by subjecting the solid small molecule organic material to the high frequency x-ray beam to provide a refined data set. FIG. 4 is a schematic of this system (100), in which an x-ray beam source device (110), a detector (120), and a processor (130) are shown.

As used herein, an "x-ray beam source device" means a device which provides high frequency x-ray beams. A "high frequency x-ray beam" means an x-ray beam, the wavelength of which is less than or equal to 1.1 angstroms, such as, e.g., less than or equal to 0.8 angstroms. Suitable x-ray beam source devices according to the present invention are as disclosed herein, including without limitation, laboratory based diffractometers that have silver or molybdenum sources.

As used herein, "total scattering data" means structure-relevant scattering data over a wide range of reciprocal space, including both Bragg scattering and diffuse scattering.

As used herein, "coupled" means connected or interfaced. The components of the system may be connected or interfaced by one or more connection or interface devices, such as, e.g., a computer, which electronically communicates with the components of the system.

Suitable detectors according to the present invention include without limitation, 2D image plate detectors as disclosed in Chupas et al. (24).

Suitable processors according to the present invention include without limitation, computers running software applications such as, e.g., PDFgetX2, RAD, FIT, PEDX, and IFO (16-19).

Data generated by subjecting the solid small molecule organic material to the high frequency x-ray beam include, but is not limited to, an associated intensity of the diffraction at a specific Bragg angle, wavelength of the x-ray beam, position of the detector used to record the intensity of the diffraction and the associated intensity of the diffraction at a specific position, and/or total scattering data.

In one aspect of this embodiment, the generated data are mathematically transformed to a reduced total scattering structure function. Preferably, the generated data are mathematically transformed to an experimentally derived atomic pair distribution function (PDF).

In another aspect of this embodiment, the solid small molecule organic material is a drug or a drug product. The solid small molecule organic material may also be crystalline, non-crystalline, amorphous, nanocrystalline, or distorted.

In a further aspect of this embodiment, the system is in compliance with the requirements of a regulatory agency, preferably the FDA. In a preferred embodiment, the system is in compliance with the requirements of 21 CFR Part 11.

The following examples are provided to further illustrate the compositions and methods of the present invention. These examples are illustrative only and are not intended to limit the scope of the invention in any way.

EXAMPLES

Example 1

Methods

Data were collected from samples of carbamezapine (CBZ) and indomethacin (IND) prepared by a melt-quenching method whereby molten compound was rapidly cooled in liquid $N_2$, lightly ground, sieved and filled into a 1 mm diameter Kapton® (Dupont, Circleville, Ohio) capillary. The laboratory data collected from a Cu K$\alpha_i$ source were collected on a Bruker-AXS D8 diffractometer using capillary transmission geometry, primary monochromated Cu K$\alpha_i$ radiation ($\lambda$=1.54056 Å) in the range 2-40°2θ, 0.016°2θ step size, 10 seconds per step at 100 K.

Crystalline materials were gently grounded to make a fine powder. The form of the crystalline material was confirmed by conventional x-ray powder diffraction. Total scattering data were collected at beamline 11ID-B at the Advanced Photon Source (APS) in Chicago using the rapid acquisition PDF method (14). Samples were sealed in 1 mm diameter kapton tubes and irradiated with x-rays of wavelength $\lambda$=0.1370 Å. A large area 2D image plate detector (MAR345) was placed centered on and perpendicular to the incident beam 198 mm behind the sample. The short wavelength is necessary to obtain data over a sufficiently high Q-range, which, in turn, is necessary to get sufficiently good resolution in real-space. Q is the magnitude of the scattering vector. Q=4πsin θ/λ, where θ is the Bragg angle. To obtain sufficient statistics in the high-Q range, multiple exposures of the image plate were made, exposing for 300 seconds, between 5 and 8 times for each data-point. The separate exposures were summed together before further processing, resulting in an integrated exposure time of 30 minutes per sample.

Under these conditions, data were obtained that could be reliably used up to a $Q_{max}$=20 Å$^{-1}$. 1D powder diffraction patterns were obtained by integrating around the Scherrer rings in the images from the image plate, correcting for beam polarization effects using the program Fit2D (15). Further processing to obtain the total scattering reduced structure function, F(Q), and the PDF, G(r), was done using the program PDFgetX2 (16).

Example 2

Total Scattering and Pdf Analysis of Carbamezapine (CBZ)

FIG. 1 summarizes the data collected from CBZ. In FIG. 1, the first row (or FIGS. 1(*a*), 1(*d*), 1(*g*), and 1(*j*)) are data collected from crystalline CBZ in the beta form, the middle row (or FIGS. 1(*b*), 1(*e*), 1(*h*), and 1(*k*)) are data collected from non-crystalline CBZ, and the bottom row (or FIGS. 1(*c*), 1(*f*), 1(*i*), and 1(*l*)) are data collected from CBZ in gamma-form. The columns have data that were measured or represented in different ways. The first column shows data from the in-house x-ray powder diffractometer collected with copper (Cu) K$\alpha$ x-ray radiation. The second column shows the PDF obtained by Fourier transforming the data in the first column. The third column is the total scattering data from the x-ray synchrotron source, plotted in the form of the reduced total scattering structure function, F(Q). The last column shows the PDF of each sample obtained by Fourier transforming the data in the third column according to the following equations:

$$G(r) = (\pi/2)\int_{Qmin}^{\infty} F(Q)\sin Qr dQ \text{ and}$$

$$F(Q) = Q\left[\frac{Ic(Q) + \langle f \rangle^2 - \langle f^2 \rangle}{\langle f \rangle^2} - 1\right].$$

wherein $Q_{min}$, is a Q value that excludes any small angle scattering intensity but includes all the wide-angle scattering (10).

The main result of the current work is self-evident in FIG. 1. Whereas the conventional XRPD measurement is not sufficient for differentiating the internal structure of the non-crystalline sample, the total scattering measurement and the resulting total scattering PDF clearly show that the non-crystalline CBZ has local packing of the beta type.

Column 1 (or FIGS. 1(*a*)-1(*c*)) shows data collected using conventional XRPD. It is evident that conventional XRPD is excellent for unambiguously differentiating between the beta (FIG. 1(*a*)) and gamma (FIG. 1(*c*)) crystalline phases of CBZ. However, conventional XRPD is insufficient for identifying and characterizing the internal structure of the non-crystalline sample, because its XRPD pattern is broad and fairly featureless (FIG. 1(*b*)). Based on this the XRPD pattern, it is not possible to characterize the non-crystalline sample as having local packing of the type seen in the beta or gamma forms, or some other form. Such a pattern generally results in a description of the sample in a non-specific way as "amorphous" or "x-ray amorphous".

As proposed by Bates et. al. (7), the conventional XRPD data can be Fourier transformed to obtain the PDF following standard methods (5, 6). Column 2 (FIGS. 1(*d*)-1(*f*)) shows the PDF data obtained by Fourier transformation of the data collected using conventional XRPD. However, the Fourier transform does not increase the information content in the data, and it is still not possible to ascertain the local packing.

Column 3 (FIGS. 1(g)-1(i)) shows total scattering F(Q) determined from data collected at the synchrotron from samples prepared in the same way as the corresponding panels in the first column. There are significant differences between FIGS. 1(g) and 1(i), indicating that F(Q) is also a valuable function for differentiating between various crystalline forms of a molecular solid, just as conventional XRPD data are for crystalline samples, even though the total scattering data were measured with much lower Q-resolution. However, more importantly, the total scattering F(Q) of the non-crystalline sample, FIG. 1(h), when measured over a wide enough range of momentum transfer and properly normalized according to the method set forth above, is now rich in information compared to the conventional measurement (FIG. 1(b)). The high-$Q_{max}$ value of 20 Å$^{-1}$ of the total scattering measurement corresponds to a real-space resolution of 0.16 Å.

The F(Q) plot of the non-crystalline sample with each of the crystalline phases can be compared. It is evident that the non-crystalline sample (FIG. 1(h)) much more closely resembles the beta-form (FIG. 1(g)) rather than the gamma form (FIG. 1(i)) in structure. Although the starting material for making the non-crystalline sample was CBZ in the gamma form, the non-crystalline sample clearly has packing more similar to the beta crystalline form than the gamma.

The same result can also be seen in the fourth column which shows the total scattering PDF, G(r), obtained by Fourier transforming the F(Q)'s in the third column. Column 4 (FIGS. 1(j)-1(l)) shows the PDF data obtained by Fourier transformation of the total scattering x-ray data. Here, it is perhaps even more clear that the non-crystalline sample (FIG. 1(k)) resembles beta form (FIG. 1(j)) in structure. There is a striking resemblance between the PDF of the beta crystalline material and the non-crystalline sample.

The correlations between PDFs in the range of r=3.0 Å-20 Å was studied. This range was chosen because the very local structure (i.e. r<3:0 Å) of all samples is the same. These are the intra-molecular pairs, for example, consisting of nearest and next-nearest neighbor carbon-carbon bonds at 1.4 Å and 2.4 Å, respectively. Comparisons of the total scattering PDFs in the range dominated by inter-molecular interactions, 3.0-20 Å, for the three samples (beta form, gamma form, and non-crystalline CBZ) using PolySNAP are shown below in Table 1.

TABLE 1

Correlation coefficients for the comparisons of total scattering PDF data using PolySNAP over the range of r = 3.0-20 Å.

|  | CBZ (beta form) | CBZ (gamma form) | CBZ (non-crystalline) |
|---|---|---|---|
| CBZ (beta form) | 1 | 0.45 | 0.84 |
| CBZ (gamma form) |  | 1 | 0.61 |
| CBZ (non-crystalline) |  |  | 1 |

The results above indicate that the noncrystalline CBZ has local packing of the beta type. PolySNAP program uses a modified version of the Spearman correlation. Additionally, a different method of comparison, the Pearson product-momentum correlation, was used on the same data set. The following formula was used to calculate Pearson product-momentum correlation, R:

$$R = \frac{1}{1-n} \sum_{i=0}^{n} \left(\frac{X_i - \overline{X}}{\sigma_x}\right)\left(\frac{Y_i - \overline{Y}}{\sigma_y}\right),$$

where $\overline{X}$ and $\sigma_x$ are the mean and standard deviation of a data set, respectively; $\overline{Y}$ and $\sigma_y$ are the mean and standard deviation of another data set, respectively; and n is the number of values in each data set. The Pearson product-momentum correlation analysis was implemented by a computer program. Comparisons of the total scattering PDFs in the range dominated by inter-molecular interactions, 3.0-20 Å, for the three samples (beta form, gamma form, and non-crystalline CBZ) using Pearson correlation are shown in Table 2.

TABLE 2

Correlation coefficients for the comparisons of total scattering PDF data using Pearson correlation over the range of r = 3.0-20 Å.

|  | CBZ (beta form) | CBZ (gamma form) | CBZ (non-crystalline) |
|---|---|---|---|
| CBZ (beta form) | 1 | 0.580032 | 0.88121 |
| CBZ (gamma form) |  | 1 | 0.721854 |
| CBZ (non-crystalline) |  |  | 1 |

The results obtained using Pearson product-momentum correlation agree with those obtained using PolySNAP.

Full-profile comparisons of the total scattering PDFs in the range dominated by inter-molecular interactions, 3-30 Å, for the three samples (beta form, gamma form, and non-crystalline CBZ) using PolySNAP (21) yielded a correlation coefficient of 0.8345 for the total scattering PDFs of the non-crystalline and beta crystalline forms (perfect match=1.0). The next closest similarity was observed for non-crystalline form of CBZ and the gamma form, but yielding a correlation coefficient of only 0.4701. Full-profile comparisons were also carried out using PolySNAP v.1.7.2 (21) over the range r 0.1-30 Å. Table 3 below shows the correlation coefficients for the profile comparisons.

TABLE 3

Correlation coefficients for the comparisons of total scattering PDF data in PolySNAP over the range of r = 0.1-30 Å.

| 100K APS data | CBZ (beta form) | CBZ (gamma form) | CBZ (non-crystalline) |
|---|---|---|---|
| CBZ (beta form) | 1 | 0.5828 | 0.9005 |
| CBZ (gamma form) |  | 1 | 0.6854 |
| CBZ (non-crystalline) |  |  | 1 |

Thus, analyzing the entire data range does not change the result significantly but reduces the sensitivity to finding differences in molecular packing of the correlation analysis by including a range of r that is highly similar regardless of the packing.

Accordingly, The results clearly demonstrate that whereas the conventional XRPD measurement is not sufficient for differentiating the internal structure of the non-crystalline sample, the total scattering measurement and the resulting PDF clearly show that the noncrystalline CBZ has local packing of the beta type.

Example 3

Identifying the Structure of a Non-Crystalline CBZ

Figure 2:
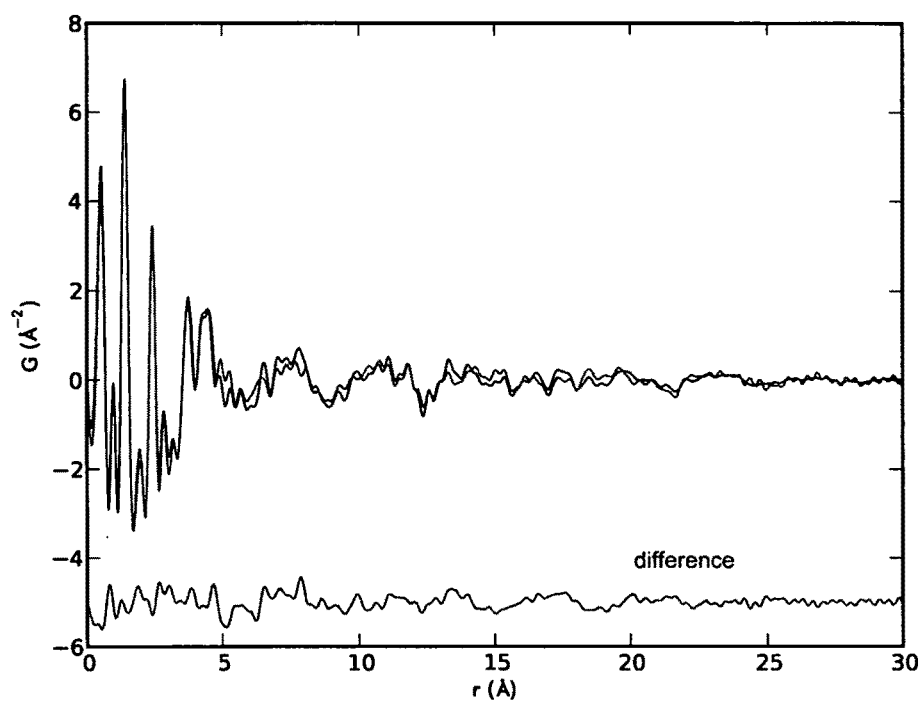
FIG. 2 shows a comparison of the total scattering atomic pair distribution function (TSPDF) from the non-crystalline sample (light grey) and the beta crystalline sample that was modified as if it were a 4.5 nm nanoparticle (dark grey). The difference between the two plots is also shown.

In FIG. 2, the agreement between the total-scattering PDFs of the bulk crystalline β-CBZ and the non-crystalline sample is shown. What is striking is that the features from the β-CBZ sample are qualitatively reproduced in the total scattering PDF of the non-crystalline sample over the whole range.

The figure was made in the following way. The total scattering PDF of the non-crystalline sample is exactly the same as that shown in FIG. 1(k) and is simply reproduced again in this figure (light grey). The total scattering PDF of the bulk (β-CBZ sample is also based on that shown in FIG. 1(j); however, it has been modified before being plotted here (dark grey). It was modified by attenuating the PDF peaks to simulate the effects of the limited range of structural coherence. If the internal atomic arrangement of a nanoparticle resembles that of a bulk crystalline analog, its PDF resembles that of the crystalline material except that the amplitude of the PDF peaks is attenuated with increasing—r due to the loss of far-neighbor correlation outside the particle. This can be modeled by multiplying the crystalline PDF with the auto-correlation of the shape function of the particle. The shape function defines the shape of the nanoparticle and has value 1 inside the surface and value 0 outside the surface of the particle. For spherical particles the form of the autocorrelation function is, or PDF characteristic function (10), is as follows (11):

$$f(r;d) = \left[1 - \frac{3r}{2d} + \frac{1}{2}\left(\frac{r}{d}\right)^3\right]\Phi(d-r)$$

where d is the diameter of the spherical particle. φ(x) is a Heaviside step function that has value 1 in the region r≤d and value 0 for r>d. What was done here was to take the measured total scattering PDF of bulk crystalline β-CBZ and multiply that by the equation listed above, where d, the nanoparticle diameter, was varied by hand until reasonable agreement was obtained over the whole range of r, as shown in FIG. 2. This agreement was obtained when a nanoparticle diameter of 4.5 nm was used.

The excellent agreement between the attenuated PDF from the bulk crystal and the "amorphous" sample total scattering PDF is dramatic proof that the local packing in the non-crystalline sample, that cannot be characterized using regular laboratory XRPD, is of the β form with a range of structural coherence of 4.5 nm.

It is interesting to ask whether the sample is made up of discrete 4.5 nm nanocrystallites of the β form or whether it is truly a homogeneous amorphous structure with short-range molecular β-like packing. The data suggest the former because the sharpness of features in the total scattering PDFs is preserved with increasing r, whilst their amplitude is simply reduced, which is not the behavior seen in truly amorphous samples. Thus, the structure of the non-crystalline CBZ sample is actually nanocrystalline β form with an average particle diameter of 4.5 nm.

Although the total scattering PDF of the non-crystalline sample is well explained by bulk β form attenuated by the PDF characteristic function for a sphere, the possibility that the sample is a dispersion of nanoparticle sizes centered around the value of 4.5 nm cannot be ruled out. For example, narrow dispersions with ~10% polydispersity are well explained using the characteristic function for a single sphere (12).

Example 4

Total Scattering And PDF Analysis Of Indomethane (IND)

Figure 3:
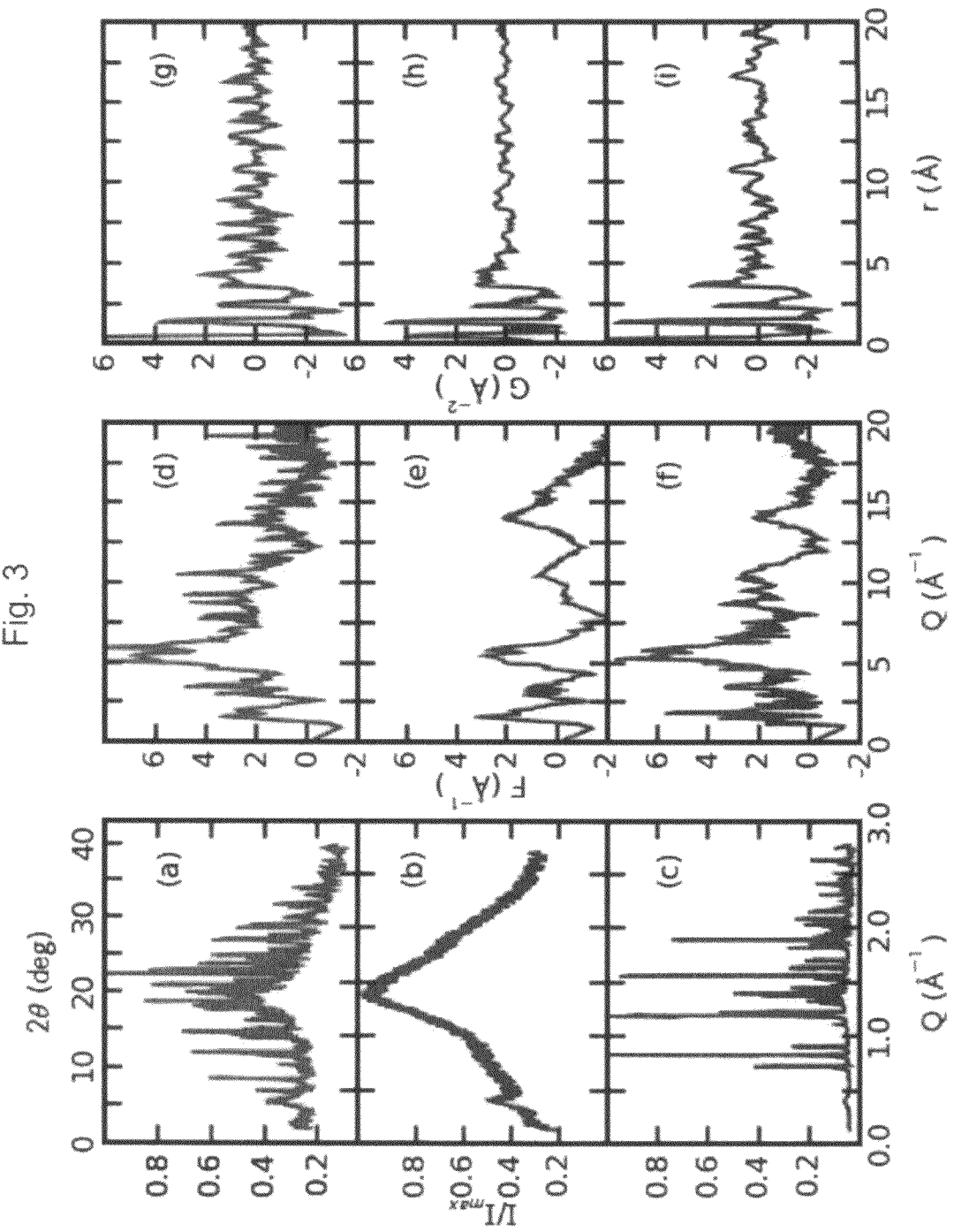
FIG. 3 shows diffraction patterns and PDFs of indomethacin (IND). The top row of panels, (FIGS. 3(a), 3(d), and 3(g)) contain patterns from IND in the αcrystalline form, the middle row (FIGS. 3(b), 3(e), and 3(h)) in the non-crystalline form and the bottom row (FIGS. 3(c), 3(f), and 3(i)) in the gamma crystalline form. The columns indicate data measured and analyzed in different ways. The first column (FIGS. 3(a), 3(b), and 3(c)) contains data from the in-house Cu $K_\alpha$ x-ray source. The second column, (FIGS. 3(d), 3(e), and 3(f)), contains the synchrotron total scattering data in the form of F(Q). The third column, (FIG. 3(g), 3(h), and (i)), contains the total scattering data in the form of the total scattering PDF, G(r), obtained by Fourier transforming the data in the third column. The non-crystalline sample can be identified as being "amorphous" from the conventional XRPD data in the first column but the total scattering data is rich in information. Unlike the CBZ, in this case the non-crystalline IND has a structure that is distinct from either of the two crystalline analogs.

The results of total scattering analysis of IND is shown in FIG. 3. IND is a widely studied molecule that can also be found in the non-crystalline form. Again, in this case the conventional XRPD data show the non-crystalline sample to be x-ray amorphous but give no indication of the local structure. In contrast, the total scattering data are rich in structural information.

Interestingly, in this case the local structure of the non-crystalline sample is distinct from either of the two crystalline samples that were measured. The local packing in the non-crystalline IND is neither the α nor the γ form but is distinct. The highest correlation coefficient from full-profile comparisons of the total scattering PDFs for melt-quenched, α and γ IND in PolySNAP was 0.6259, returned for the melt-quenched and α-IND phases. This is significantly lower than the highest value obtained for the CBZ total scattering PDF comparisons, with all other coefficients less than 0.5. When the comparison is performed over the range of r of 3.0-20 Å (shown in Table 4 below), the results are similar.

TABLE 4

Correlation coefficients for the comparisons of total scattering PDF data using PolySNAP over the range of r = 3.0-20 Å.

|  | IND (alpha form) | IND (gamma form) | IND (non-crystalline) |
|---|---|---|---|
| IND (alpha form) | 1 | 0.4075 | 0.6784 |
| IND (gamma form) |  | 1 | 0.4911 |
| IND (non-crystalline) |  |  | 1 |

Additionally, Pearson correlation was performed over the range of r of 3.0-20 Å. The correlation coefficients are shown below in Table 5.

TABLE 5

Correlation coefficients for the comparisons of total scattering PDF data using Pearson correlation over the range of r = 3.0-20 Å.

|  | IND (alpha form) | IND (gamma form) | IND (non-crystalline) |
|---|---|---|---|
| IND (alpha form) | 1 | 0.477629 | 0.706309 |
| IND (gamma form) |  | 1 | 0.648231 |
| IND (non-crystalline) |  |  | 1 |

Thus, the total scattering PDFs indicate that the local structure of the melt-quenched IND sample at 100 K is largely distinct from the α and γ crystalline forms. This contrasts with the suggestion based on crystallization and spectroscopic investigations that below Tg (315K) (22) amorphous IND has local structure, with dimeric hydrogen bonding, similar to the γ form (23). Linear combinations of the α and γ crystalline phases did not give good agreement with the total scattering PDF from the non-crystalline sample. However, this result shows that distinct local molecular packing arrangements are possible in the non-crystalline phase, and that the total scattering PDF can characterize them. As with the non-crystalline CBZ sample, oscillations of the non-crystalline IND sample in the PDF are apparent over the whole r-range shown and clearly extend beyond 20 Å, which show that the non-crystalline IND sample is also nanocrystalline rather than truly amorphous.

These results have a number of important implications. First, total scattering using short wavelength x-rays produces data that can be used to differentiate different forms of amorphous or nanocrystalline molecular solids. This is therefore an approach that can take the role in amorphous pharmaceuticals that x-ray powder diffraction plays for crystalline powders: that of fingerprinting structural forms. This will greatly facilitate the commercialization of drugs in amorphous and nanocrystalline forms. It will also aid research into the amorphous and nanocrystalline forms of pharmaceuticals and other molecular solids because in both the cases studied here, and by extension many cases, sufficient information exists in the total scattering signal to fit well-defined structural models for the molecular conformation and packing. This opens the door to future studies of things such as phase stability and the effects of process history on the form in non-crystalline solid molecular solids. For example, in the case of carbemazepine, the non-crystalline form studied here had β-packing, despite being derived from a γ-form precursor. Interestingly, on heating the amorphous structure recrystallizes into γ-CBZ. Thus, x-ray total scattering analysis may help pharmaceutical scientists also find new crystalline polymorphs via an amorphous or nanocrystalline route.

Example 5

Stability Testing of Drug

Drug A shows polymorphism. The desired form of Drug A is a nanocrystalline form (a). This nanocrystalline form and other forms of Drug A have different property in terms of solubility, stability, and/or melting point. Because of these differences in property, Drug A's safety, performance and/or efficacy are affected. Unfortunately, drug product performance testing, such as tests assessing the rate of dissolution, does not provide adequate control if polymorph ratio changes.

In conventional XRPD, α-nanocrystalline form of Drug A shows up as a broad featureless peak. In contrast, x-ray total scattering analysis of the α-nanocrystalline form of Drug A and the mathematical transformation of the data generated from such analysis show definite peaks and thus give a fingerprint to identify this solid form of Drug A. Therefore, appropriate acceptance criteria, such as numerical limits for the position of the peaks, numerical ranges for the intensity of the peak, or other criteria may be specified.

Drug A in α-nanocrystalline form is subjected to a variety of environmental factors, such as temperature, humidity, and light, and then subjected to a variety of tests, including x-ray total scattering analysis, to examine how the quality of a drug substance or drug product varies with time under the influence of these environmental factors. From this information, especially data from x-ray total scattering analysis and the mathematical transformation of that data, the drug manufacturer can establish a retest period for the drug, or a shelf life for the drug product and recommended storage conditions.

Stability information gathered from x-ray total scattering analysis may be submitted to the FDA for the purposes of submitting an investigational new drug application. For example, 21 CFR 312.23 requires the reporting of chemistry, manufacturing, and control information. In each phase of the investigation, sufficient information is required to be submitted to assure the proper identification, quality, purity, and strength of the investigational drug. Stability data are required in all phases of the investigational new drug application to demonstrate that the new drug substance and drug product are within acceptable chemical and physical limits for the planned duration of the proposed clinical investigation.

Stability information gathered from x-ray total scattering analysis may also be submitted to the FDA for the purposes of application for FDA approval to market a new drug. For example, 21 CFR 314.50 requires "[a] full description of the drug substance including its physical and chemical characteristics and stability; . . . and the specifications necessary to ensure the identity, strength, quality, and purity of the drug substance and the bioavailability of the drug products made from the substance, including, for example, tests, analytical procedures, and acceptance criteria relating to stability, sterility, particle size, and crystalline form." X-ray total scattering analysis and the mathematical transformation of the data generated by such analysis are used to provide stability and acceptance criteria relating to Drug A in the nanocrystalline form for the approval process, while conventional x-ray powder diffraction techniques is not be able to provide this information.

Furthermore, stability information gathered using x-ray total scattering analysis is submitted to the FDA and for the purposes of complying with good manufacturing practice for finished pharmaceuticals, for example, the requirements of 21 CFR 211.137 (expiration dating), 211.166 (stability test), 211.170 (testing of reserved samples), and 211.194 (maintenance of laboratory records, including stability test results).

Example 6

Manufacturing Process Control

Drug B shows polymorphism. The desired form of Drug B is a nanocrystalline form. The manufacturing process does not routinely give this nanocrystalline form of Drug B. This nanocrystalline form and other forms of Drug B have different property in terms of solubility, stability, and/or melting point. Because of these differences in property, Drug B's safety, performance and/or efficacy are affected. Unfortunately, drug product performance testing, such as tests assessing the rate of dissolution, does not provide adequate control if polymorph ratio changes.

In conventional XRPD, the nanocrystalline form of Drug B shows up as a broad featureless peak. In contrast, x-ray total scattering analysis of the nanocrystalline form of Drug B and the mathematical transformation of the data generated from such analysis shows definite peaks and thus gives a fingerprint to identify this solid form of Drug B. Therefore, the manufacturer can specify appropriate acceptance criteria, such as numerical limits for the position of the peaks, numerical ranges for the intensity of the peak, or other criteria.

Representative samples of different batches of drug are tested, including x-ray total scattering, to determine the solid form. Batches that do not conform to the specification are rejected.

This information may be submitted to the FDA for the purposes of submitting an investigational new drug application, for example 21 CFR 312.23; for the purposes of application for FDA approval to market a new drug, for example, the requirements of 21 CFR 314.50(d)(1); and for the purposes of complying with good manufacturing practice for finished pharmaceuticals, for example, the requirements of 21 CFR 211.84, 211.110, 211.160, and 211.194.

Example 7

Submission of Patent Information

Drug C shows polymorphism. During research and development, the manufacturer of Drug C generates three nanocrystalline forms of Drug C. These particular nanocrystalline forms are only distinguishable by total scattering X-ray analysis and the mathematical transformation of data generated from such analysis, because all three forms show similar broad, featureless peaks in conventional XRPD. The manufacturer submits a new drug application with respect to Drug C in the α-nanocrystalline form. The manufacturer also has test data of Drug C (including those set forth in 21 CFR 314.53(b)(2)) in the β- and γ-nanocrystalline forms. The test data demonstrate that a drug product containing the β-nanocrystalline form perform the same as the drug product described in the new drug application, but the γ-nanocrystalline form of Drug C does not. The manufacturer of Drug C has patented all three nanocrystalline forms of Drug C.

The manufacturer submits the patent information (which includes x-ray total scattering analysis of these nanocrystalline forms and/or the mathematical transformation of the data from such analysis) of both the α- and β-nanocrystalline forms of Drug C to the United States Food and Drug Administration (FDA). For example, this information may be submitted in compliance with the requirements of 21 CFR 314.53 for patents that claim a polymorph that is the same as the active ingredient described in the approved or pending application. The manufacturer certifies that it has test data, as set forth in 21 CFR 314.53(b)(2), demonstrating that a drug product containing the polymorph perform the same as the drug product described in the new drug application. Upon approval of Drug C in the α-nanocrystalline form, the patent information for both the α- and β-nanocrystalline forms of Drug C is listed in the Orange Book.

Example 8

Abbreviated New Drug Application

Section 505(j)(2) of the Federal Food, Drug, and Cosmetic Act (the "Act") specifies that an Abbreviated New Drug Application (ANDA) must contain, among other things, information to show that the active ingredient in the generic drug product is the "same as" that of the Reference Listed Drug (RLD). Under section 505(j)(4) of the Act, FDA must approve an ANDA unless the agency finds, among other things, that the ANDA contains insufficient information to show that the active ingredient is the same as that in the RLD. FDA regulations implementing section 505(j) of the Act provide that an ANDA is suitable for consideration and approval if the generic drug product is the "same as" the RLD. Specifically, 21 CFR 314.92(a)(1) provides that the term "same as" means, among other things, "identical in active ingredient(s)." The drug substance in a generic drug product is considered to be the same as the drug substance in the RLD if it meets the same standards for identity. While using a drug substance polymorphic form that is different from that of the RLD may not preclude an ANDA applicant from formulating a generic drug product that exhibits bioequivalence and stability, the FDA recommends that ANDA applicants still consider the influence of polymorphic forms, because they affect bioavailability, bioequivalence, and stability.

A. Generic Drug with the Same Solid State Structure Form

Drug D exhibits polymorphism. Different polymorphs of Drug D exhibit different solubilities. The active ingredient of the final product is a nanocrystalline form of Drug D, which exhibits a broad featureless peak under conventional XRPD analysis. Generic manufacturer is able to make the same nanocrystalline form of Drug D, as determined by x-ray total scattering analysis and the mathematical transformation of the data generated from such analysis. The generic manufacturer submits an ANDA in accordance with 21 CFR 314.94. The ANDA contains, among other information, x-ray total scattering analysis of the proposed generic version of Drug D, demonstrating that the proposed generic has the same form as the approved form.

B. Generic Drug with Different Solid State Structure Form

Drug E exhibits polymorphism. Different polymorphs of Drug E exhibit different solubilities. The α-crystalline and β-crystalline forms of Drug E are not highly soluble, as defined by Biopharmaceutics Classification System (BCS) criteria (not soluble in less than or equal to 250 ml water over a pH range of 1 to 7.5). The β-nanocrystalline form of Drug E is more soluble than the crystalline forms, but still is not highly soluble, as defined by BCS criteria. The approved drug product contains the β-nanocrystalline form of Drug E. Generic manufacturer is able to develop and manufacture an α-nanocrystalline form of Drug E and is able to show that the α-nanocrystalline form of Drug E is the same as the β-nanocrystalline form of Drug E in bioavailability and bioequivalence studies.

There is no polymorph specification in the United States Pharmacopeia (USP) (for example, melting point). There is sufficient concern that a polymorph specification in the drug product be established, and drug product performance testing (e.g., dissolution testing) does not provide adequate controls if the polymorph ratio changes. Thus, the generic manufacturer has to set specification with respect to the α-nanocrystalline form of Drug E. This information may be used for stability testing and manufacturing process control, as exemplified in Examples 5 and 6 above.

In conventional XRPD, both nanocrystalline forms of Drug E exhibit a broad featureless peak. X-ray total scattering analysis of the two nanocrystalline form of Drug E and the mathematical transformation of the data generated from such analysis show different peaks and thus give a fingerprint to identify these solid forms of Drug E. Therefore, the generic manufacturer can differentiate between the two nanocrystalline forms and specify appropriate acceptance criteria for the α-nanocrystalline form of Drug E, such as numerical limits for the position of the peaks, numerical ranges for the intensity of the peak, or other criteria.

Once an acceptance standard is specified, the generic manufacturer can conduct stability and manufacturing process controls as set forth in the above examples. This information is used by the generic manufacturer to the FDA in an ANDA, in compliance with the requirements 21 CFR 314.94. Among other information, 21 CFR 314.94 requires chemistry, manufacturing and control information, including requirements of 21 CFR 314.50(d)(1)(i), "[a] full description of the drug substance including its physical and chemical characteristics and stability; . . . the process controls used during manufacture and packaging; and the specifications necessary to ensure the identity, strength, quality, and purity of the drug substance and the bioavailability of the drug products made from the substance, including, for example, tests, analytical procedures, and acceptance criteria relating to stability, sterility, particle size, and crystalline form." With data generated from x-ray total scattering analysis and mathematical transformations of such data, the manufacturer is able to comply with these FDA requirements.

Example 9

An Integrated System for Characterizing a Solid Small Molecule Organic Material

An integrated system for characterizing a solid small molecule organic material may be designed. This integrated system may be designed for fully automated measurement, analysis and reporting in an easy to use package suitable for a multi-disciplinary environment. Once the user of the system place a sample of a solid small molecule organic material into the appropriate chamber of the system and indicates to the system as such, the system will perform the x-ray total scattering analysis, collect the data generated thereby, and mathematically transforming the generated data to provide a refined dataset. Depending on the user's preference, the generated data may be mathematically transformed to a reduced total scattering structure function, or an experimentally derived atomic pair distribution.

The system may have extensive uses in the pharmaceutical industry, especially drug development. It can be used to provide a unique profile (a "fingerprint") for a drug or a drug product, whether such drugs or drug products are amorphous, crystalline, nanocrystalline, or distorted. The system may further be programmed to search for similar fingerprints in a library of fingerprints of known compounds so that the drug or drug products may be identified.

Furthermore, the system may be designed to meet the requirements of 21 CFR Part 11. Software may be installed such that the system can keep track of audit trail records. The audit trail records will be stored in a central server database and will always active and cannot be bypassed. Audit trail records will include the following information: application login/logoff, unauthorized attempts handling, start/stop instrument sessions, and new/changed electronic records. The audit trail record will further contain the following data, if applicable: event type, user ID, full (printed) user name, date/time, electronic record checksum, electronic record identification, additional data such as sample name and sample ID. Checksum algorithms, which detect accidental errors that may have been introduced during its transmission or storage, are known in the art. The reporting functionality of the audit trail software ensures reliable copying and readability by the FDA.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

CITED DOCUMENTS

All documents cited herein, including those identified below, are incorporated by reference as if recited in full herein:

1. W. I. F. David, K. Shankland, L. B. McCusker, and C. Baerlocher, editors, *Structure Determination from Powder Diffraction Data*, Oxford University Press, Oxford, 2002.
2. H. M. Rietveld, J. Appl. Crystallogr. 2, 65 (1969).
3. J. Bernstein, *Polymorphism in molecular crystals*, Oxford University Press, Oxford, 2002.
4. S. J. L. Billinge and I. Levin, Science 316, 561 (2007).
5. B. E. Warren, *X-ray diffraction*, Dover, N.Y., 1990.
6. T. Egami and S. J. L. Billinge, *Underneath the Bragg peaks: structural analysis of complex materials*, Pergamon Press, Elsevier, Oxford, England, 2003.
7. S. Bates, G. Zografi, D. Engers, K. Morris, K. Crowley, and A. Newman, Pharmaceut. Res. 23, 2333 (2006).
8. A. C. Wright, Glass. Phys. Chem. 24, 148 (1998).
9. S. J. L. Billinge, J. Solid State Chem. 181, 1698 (2008).
10. C. L. Farrow and S. J. L. Billinge, Acta Crystallogr. A 65, 232 (2009).
11. K. Kodama, S. Iikubo, T. Taguchi, and S. Shamoto, Acta Crystallogr. A 62, 444 (2006).
12. A. S. Masadeh, E. S. Božin, C. L. Farrow, G. Paglia, P. Juhás, A. Karkamkar, M. G. Kanatzidis, and S. J. L. Billinge, Phys. Rev. B 76, 115413 (2007).
13. S. Brühne, E. Uhrig, K.-D. Luther, W. Assmus, M. Brunelli, A. S. Masadeh, and S. J. L. Billinge, Z. Kristallogr. 220, 962 (2005).
14. P. J. Chupas, X. Qiu, J. C. Hanson, P. L. Lee, C. P. Grey, and S. J. L. Billinge, J. Appl. Crystallogr. 36, 1342 (2003).
15. A. P. Hammersley, Fit2d v9.129 reference manual v3.1, ESRF Internal Report ESRF98HA01T, 1998.
16. X. Qiu, J. W. Thompson, and S. J. L. Billinge, J. Appl. Crystallogr. 37, 678 (2004).
17. V. Petkov, "A program for analysis of XRD data from amorphous materials for P/C's", J. Appl. Cryst. 22, 387 (1989).
18. V. Petkov et al. Phys. Rev. Lett. 83, 4089 (1999).
19. V. Petkov et al. Phys. Rev. Lett. 85, 3436 (2000).
20. S. Bates et al., "Analysis of Amorphous and Nanocrystalline Solids from Their X-Ray Diffraction Patterns", Pharmaceutical Research, 23, 2333 (2006).
21. G. Barr, W. Dong and C. J. Gilmore, Journal of Applied Crystallography, 2004, 37, 658-664.
22. V. Andronis and G. Zografi, Journal of Non-Crystalline Solids, 2000, 271, 236-248.
23. E. Y. Shalaev and G. Zografi, in Amorphous food and pharmaceutical systems, ed. Harry Ed Levine, Royal Society of Chemistry, Cambridge, 2002, pp. 11-30.
24. Chupas et al., Rapid-acquisition pair distribution function (RA-PDF) analysis, J. Appl. Cryst., 2003, 36, 1342-1347.
25. Barr et al., PolySNAP: a computer program for analysing high-throughput powder diffraction data, J. Appl. Cryst., 2004, 37, 658-664.

What is claimed is:

1. A method of reliably characterizing an amorphous material, the method comprising:
   subjecting the amorphous material to x-ray beams having a wavelength less than or equal to 1.1 angstroms such that x-ray data is scattered from the amorphous material,
   collecting the scattered x-ray data over reciprocal lattice vector of at least 8.5 inverse angstroms,
   deriving an atomic pair distribution function (PDF) from the collected x-ray data, mathematically transforming the derived PDF data to a reduced total scattering structure function, and
   reliably determining structural information of the amorphous material.

2. The method of claim 1, wherein the x-ray beam source is a synchrotron.

3. The method of claim 2, wherein the amorphous material is subjected to the synchrotron for a period of about 30 minutes.

4. The method of claim 1, wherein the x-ray beam has a wavelength less than or equal to 0.8 angstroms.

5. The method of claim 1, wherein the collecting step includes collecting data over a range of different Bragg angles.

6. The method according to claim 1, wherein the amorphous material is a drug or a drug product.

7. The method according to claim 1, wherein the structural information is a phase of the amorphous material.

8. The method according to claim 1, wherein the structural information is differentiating local molecular packaging arrangements.

9. The method according to claim 1, wherein the structural information is a level of stability of the amorphous material.

10. The method according to claim 1, wherein structural information is the three-dimensional arrangement of atoms that constitute the amorphous material.

11. A method of reliably characterizing a nanocrystalline molecular solid, the method comprising:
    subjecting a nanocrystalline molecular solid having no more than 3 nm in length to x-ray beams having a wavelength less than or equal to 1.1 angstroms such that x-ray data is scattered from the amorphous material,
    collecting the scattered x-ray data over a reciprocal lattice vector of above 8.5 inverse angstroms,
    deriving an atomic pair distribution function (PDF) from the collected x-ray data, mathematically transforming the derived PDF data to a reduced total scattering structure function, and
    reliably determining structural information of the amorphous material.

12. The method of claim 11, wherein the structural information includes differentiating the nanocrystalline molecular solid from an amorphous solid.

13. The method of claim 11, wherein the nanocrystalline molecular solid has a defined structure over local and intermediate ranges of about 10 angstroms.

14. The method according to claim 11, wherein the structural information is a phase of the nanocrystalline molecular solid material.

15. The method according to claim 11, wherein the structural information is differentiating local molecular packaging arrangements.

16. The method according to claim 11, wherein the structural information is a level of stability of the nanocrystalline molecular solid.

17. The method according to claim 11, wherein structural information is the three-dimensional arrangement of atoms that constitute the nanocrystalline molecular solid.

18. The method according to claim 11, wherein structural information is a level of crystallinity of the nanocrystalline molecular solid.

19. The method according to claim 11, wherein the structural information includes a first structural information and a second structural information.

20. The method of claim 19, wherein the first structural information is structural information of the nanocrystalline molecular solid at a first storage time or condition, and second structural information is structural information nanocrystalline molecular solid at a second storage time or condition.

21. The method of claim 20, wherein the nanocrystalline molecular solid is a drug, and further wherein the method can detect changes in the structural information of the drug during manufacturing, packaging, distribution, or storage of the drug.

22. The method of claim 20, wherein the condition is selected from the group consisting of temperature, pressure, pH, humidity, light, chemical composition of the atmosphere, and combinations thereof.

23. The method of claim 20, wherein the nanocrystalline molecular solid is a drug, and further wherein the method can detect changes in stability of the drug during manufacturing, packaging, distribution, or storage of the drug.

24. A method for seeking marketing approval for a nanocrystalline pharmaceutical drug,
    submitting structural information relating to the nanocrystalline pharmaceutical drug to a regulatory agency, wherein the structural information is generated from the method of claim 11.

25. The method according to claim 24, wherein the regulatory agency is the United States Food and Drug Administration (FDA).

26. The method according to claim 25, wherein the submission is made in an investigational new drug application, an application for FDA approval to market a new drug (NDA), an abbreviated new drug application, or in relation to maintaining the identity or quality of the solid drug.

* * * * *